United States Patent
Mroczkiewicz et al.

(10) Patent No.: US 11,072,619 B2
(45) Date of Patent: Jul. 27, 2021

(54) PYRAZOLE[1,5-A] PYRIMIDINE DERIVATIVES AS KINASE JAK INHIBITORS

(71) Applicant: CELON PHARMA S.A., Kielpin/Lomianki (PL)

(72) Inventors: Michal Mroczkiewicz, Warsaw (PL); Bartosz Stypik, Mlawa (PL); Anna Bujak, Bialogard (PL); Krzysztof Szymczak, Lodz (PL); Pawel Gunerka, Warsaw (PL); Krzysztof Dubiel, Warsaw (PL); Maciej Wieczorek, Kielpin/Lomianki (PL); Jerzy Pieczykolan, Warsaw (PL)

(73) Assignee: Celon Pharma S.A., Kielpin/Lomianki (PL)

( * ) Notice: Subject to any disclaimer, the term of this patent is extended or adjusted under 35 U.S.C. 154(b) by 0 days.

(21) Appl. No.: 16/609,891

(22) PCT Filed: May 10, 2018

(86) PCT No.: PCT/EP2018/062164
§ 371 (c)(1),
(2) Date: Oct. 31, 2019

(87) PCT Pub. No.: WO2018/206739
PCT Pub. Date: Nov. 15, 2018

(65) Prior Publication Data
US 2020/0199128 A1    Jun. 25, 2020

(30) Foreign Application Priority Data
May 12, 2017    (PL) .......................................... 421576

(51) Int. Cl.
*C07D 487/04* (2006.01)
(52) U.S. Cl.
CPC .................. *C07D 487/04* (2013.01)
(58) Field of Classification Search
CPC .................................................... C07D 487/04
USPC ..................................................... 514/233.2
See application file for complete search history.

(56) References Cited

FOREIGN PATENT DOCUMENTS

| WO | WO 2011/003065 A2 | 1/2011 |
|---|---|---|
| WO | WO 2012/125893 A1 | 9/2012 |
| WO | WO 2014/039595 A1 | 3/2014 |
| WO | WO 2015/118434 A1 | 8/2015 |

OTHER PUBLICATIONS

International Search Report dated Jul. 20, 2018 in connection with PCT International Application No. PCT/EP2018/062164.
Written Opinion (form PCT/ISA/237) dated Jul. 20, 2018 in connection with PCT International Application No. PCT/EP2018/062164.

*Primary Examiner* — Kahsay Habte
(74) *Attorney, Agent, or Firm* — Gary J. Gershik; Cooper & Dunham LLP

(57) ABSTRACT

A compound or its acid addition salt of the general formula (I), wherein $R_1$ represents phenyl substituted with one or two substituents selected from the group consisting of halogen and C1-C3 alkoxyl, or 6-membered heteroaryl with 1 or 2 nitrogen atoms, which is unsubstituted or substituted with a substituent selected from the group consisting of $-NH_2$, halogen, alkyl C1-C4, alkoxyl C1-C3, and 6-membered heterocyclyl comprising 1 or 2 heteroatoms selected from the group consisting of N and O. The compound has the activity of kinase JAK1/JAK3 inhibitor and can find use in the treatment of chronic inflammatory and autoimmunological diseases.

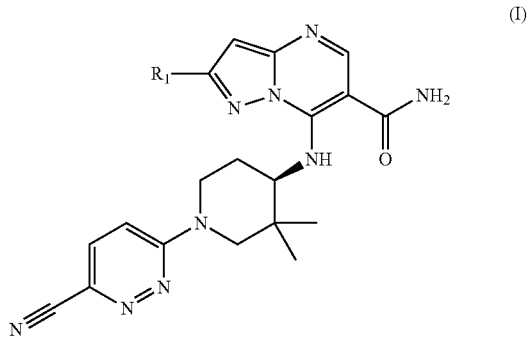

20 Claims, No Drawings

PYRAZOLE[1,5-A] PYRIMIDINE DERIVATIVES AS KINASE JAK INHIBITORS

CROSS-REFERENCE TO RELATED APPLICATIONS

This application is a § 371 national stage of PCT International Application No. PCT/EP2018/062164, filed May 10, 2018, claiming priority of Polish Patent Application No. PL421576, filed May 12, 2017, the contents of each of which are hereby incorporated by reference into the application.

FIELD OF THE INVENTION

The invention relates to novel compounds, pyrazolo[1,5-a]pyrimidine derivatives showing the activity of tyrosine kinase JAK, in particular JAK1/JAK3, inhibitors. The compounds can find use in the treatment of diseases, in the pathogenesis of which are involved kinases JAK1 and JAK3. In particular, the compounds can find use as immunological response modulators, for example as immunosuppressants in the field of transplantology, and in the treatment of autoimmunological and inflammatory diseases.

PRIOR ART

Janus kinases JAK are a family of non-receptor tyrosine kinases that are involved in intracellular transduction of cytokines and chemokines induced signal in the JAK-STAT signaling pathway. They play significant role in the activation of STAT proteins and initiation of genes transcription, among others genes encoding inflammation mediators. The activity of transcriptional factor STAT in a cell depends on its phosphorylation level. Increase of phosphorylation level in a cell depends on kinases JAK activity; inhibition of kinases causes decrease of phosphorylation and transcriptional activity of STAT proteins and in consequence reduction of expression of regulated genes. Therefore, kinases JAK inhibitors block specific signalling pathway responsible for induction and maintenance of inflammatory state that underlies autoimmunological diseases. It has been repeatedly confirmed that cytokines involved in development and clinical course of inflammatory diseases activate JAK-STAT pathway, this making the latter important element in development and clinical course of such diseases like rheumatoid arthritis, psoriasis and asthma. Stimulation of JAK kinases in lymphocytes T induced by pro-inflammatory cytokines leads to activation of STAT transcription factor. This affects differentiation of lymphocytes T that stimulate lymphocytes B to enhance production of immunoglobulins E and are responsible for eosinophils recruitment and maturation, this leading to development of local inflammatory response. Due to blocking phosphorylation of STAT factor, kinase JAK inhibitors can inhibit differentiation of lymphocytes T population and inflammatory response and hence can be useful as in the treatment of inflammatory diseases.

JAK family comprises 4 known members, JAK1, JAK2, JAK3 and TYK2. Kinases JAK1, JAK2 and TYK2 are expressed ubiquitously, while kinase JAK3 is primarily expressed in hematopoietic cells. Thus it is believed that the effects of JAK3 inhibition will be limited to immunological system. JAK3 is activated by interleukines IL2, IL4, IL7, IL9, IL15 and IL21 via transmembrane γc receptor. Similarly as JAK3, JAK1 is associated with IL-2 receptor and together with JAK3 mediates IL-2 signalling cascade to regulate T cells proliferation. JAK1 plays also the role in IL-6 and IFN-gamma signalling, associated with inflammatory response. JAK3 and/or JAK1 inhibitors are an interesting target in the search of medicaments that can find use as immunological response modulators, in particular for preventing transplants rejections in transplantology and in the treatment of autoimmunological and inflammatory diseases.

Compounds that exhibit the activity of kinases JAK1 and/or JAK3 inhibition, especially selective over JAK2, are searched for.

WO 2014/039595A1 discloses compounds with imidazo[1,2-b]pyridazine-6-carboxamide core of the formula

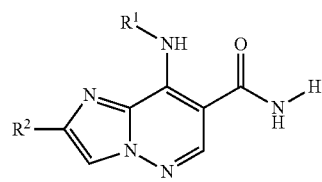

as JAK3 and/or JAK1 inhibitors selective over JAK2 and potential medicaments for the treatment of chronic inflammatory and autoimmunological diseases.

WO2012/125893 discloses compounds with pyrrolo[1,2-b]pyridazine-6-carboxamide core of the formula

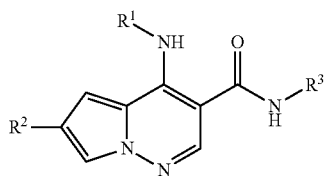

as JAK3 and/or JAK1 inhibitors selective over JAK2 and potential medicaments for the treatment of chronic inflammatory and autoimmunological diseases.

WO2012/125886 discloses compounds with pyrrolo[1,2-b]pyridazine-6-carboxamide core of the formula

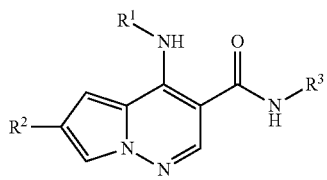

as JAK3 and/or JAK1 inhibitors selective over JAK2 and potential medicaments for the treatment of chronic inflammatory and autoimmunological diseases.

WO2011/014817 discloses JAK3 inhibitors compounds with bicyclic heterocyclic core of the formula

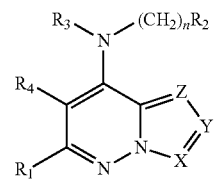

only derivatives with pyrrolo[1,2-b]pyridazine-6-carboxamide core being disclosed as specific compounds.

US2010/0105661 discloses compounds with pyrrolo[2,3-b]pyridine core of the formula

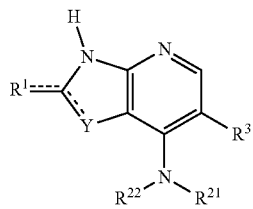

as kinase JAK3 inhibitors for use in diseases associated with undesired or abnormal cytokines signal transduction.

SUMMARY OF THE INVENTION

There is a need for new compounds exhibiting the ability of kinase JAK inhibition of high efficacy and/or selectivity that potentially could be useful in the treatment of inflammatory and autoimmunological diseases. This problem is solved by the present invention.

The object of the invention is a compound of the general formula (I)

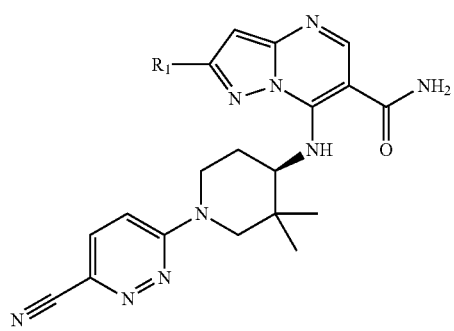

wherein $R_1$ represents:
phenyl substituted with one or two substituents selected from the group consisting of halogen and C1-C3 alkoxy; or
6-membered heteroaryl with 1 or 2 nitrogen atoms, which is unsubstituted or substituted with a substituent selected from the group consisting of:
$NH_2$,
halogen,
alkyl C1-C4,
alkoxyl C1-C3, and
6-membered heterocyclyl comprising 1 or 2 heteroatoms selected from the group consisting of N and O,
or its acid addition salt.

The compounds of the formula (I) have the ability of selective inhibition of kinases JAK3 and/or JAK1 over JAK2 and can find use in the treatment of autoimmunological and inflammatory diseases.

In a further aspect, the invention relates also to the compound of the formula (I) as defined above for use as a medicament.

In a further aspect, the invention relates also to a pharmaceutical composition comprising the compound of the formula (I) as defined above.

In a further aspect, the invention relates also to the use of the compound of the formula (I) as defined above for the preparation of a medicament for use in the treatment of autoimmunological and inflammatory diseases.

In a further aspect, the invention relates also to a method of treatment of autoimmunological and inflammatory diseases in a mammal subject that comprises administering to said subject a therapeutically effective amount of the compound of the formula (I) as defined above.

In a further aspect, the invention relates also to the compound of the formula (I) as defined above for use in a method of treatment of autoimmunological and inflammatory diseases in a mammal subject.

DETAILED DESCRIPTION OF THE INVENTION

Preferred embodiments of the invention are described in the following detailed description and attached claims. Various aspects of the invention are defined herein in more detail. Each of the aspects thus defined may be combined with any other aspect or aspects, unless clearly indicated otherwise. In particular, any feature indicated as a preferred or advantageous one may be combined with any other feature or features indicated as a preferred or advantageous one.

Reference throughout the description to "one of the embodiments" or "an embodiment" means that a particular feature, structure or characteristics described in connection with this embodiment is comprised in at least one embodiment of the present invention. Thus any occurrences of the phrase "in one embodiment" or "in an embodiment" in various parts of the present description not necessarily relate to the same, but can. Furthermore, particular features, structures or characteristics can be combined in any suitable manner, as will be appreciated for a person skilled in the art of this disclosure, in one or more embodiments. Furthermore, although some embodiments described herein encompass some but not other features comprised in other embodiments, combinations of features of various embodiments can be encompassed by the scope of the invention and form various examples of embodiments, as will be appreciated by a person skilled in the art. For, example, in the attached claims any of claimed embodiment may be used in any combination.

In a first aspect, the invention provides a compound of the following formula (I)

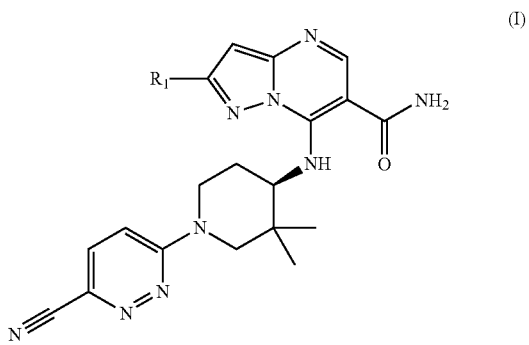

wherein $R_1$ represents:
phenyl substituted with one or two substituents selected from the group consisting of halogen and C1-C3 alkoxy; or 6-membered heteroaryl with 1 or 2 nitrogen atoms, which is unsubstituted or substituted with a substituent selected from the group consisting of:
NH$_2$,
halogen,
alkyl C1-C4,
alkoxyl C1-C3, and
6-membered heterocyclyl comprising 1 or 2 heteroatoms selected from the group consisting of N and O;
or its acid addition salt.

In one embodiment of the invention, $R_1$ represents phenyl substituted with one or two substituents selected from the group consisting of halogen atom and C1-C3 alkoxyl.

In an embodiment of the invention, $R_1$ represents phenyl substituted with one or two halogen atom, preferably one or two fluorine atoms. Advantageously, $R_1$ represents phenyl substituted with one fluorine atoms. Also advantageously, $R_1$ represents phenyl substituted with two fluorine atoms.

In another embodiment of the invention, $R_1$ represents phenyl substituted with one or two C1-C3 alkoxyl groups, preferably methoxy groups, especially with one methoxy group, including 2-methoxyphenyl, 4-methoxyphenyl and 5-methoxyphenyl, in particular 4-methoxyphenyl and 5-methoxyphenyl.

In an embodiment of the invention, $R_1$ represents phenyl substituted with one halogen atom, preferably one fluorine atom, and one C1-C3 alkoxy group, especially methoxy. Advantageously $R_1$ represents phenyl substituted with one fluorine atom and one methoxy groups. Examples of such substitution include 2-fluoro-5-methoxyphenyl and 2-fluoro-4-methoxyphenyl, especially 2-fluoro-5-methoxyphenyl.

In another embodiment of the invention, $R_1$ represents 6-membered heteroaryl, comprising 1 or 2 nitrogen atoms, unsubstituted or substituted by a substituent selected from the group consisting of NH2; halogen; C1-C4 alkyl; C1-C3 alkoxyl; and 6-membered heterocyclyl comprising 1 or 2 heteroatoms selected from the group consisting of N and O.

In one embodiment, $R_1$ represents unsubstituted 6-membered heteroaryl, in particular pyridinyl or pyrimidinyl.

In another embodiment, $R_1$ represents 6-membered heteroaryl, in particular pyridinyl or pyrimidinyl, substituted by a substituent selected from the group consisting of NH$_2$; halogen; C1-C4 alkyl; C1-C3 alkoxyl; and 6-membered heterocyclyl comprising 1 or 2 heteroatoms selected from the group consisting of N and O.

In particular, 6-membered heteroaryl mentioned above, preferably pyridinyl or pyrimidinyl, is substituted by a substituent selected from the group consisting of NH$_2$; halogen, especially fluorine; C1-C4 alkyl, especially methyl or ethyl; C1-C3 alkoxyl, especially methoxyl or ethoxyl; and 6-membered heterocyclyl comprising 1 or 2 heteroatoms selected from the group consisting of N and O, especially 4-morpholinyl. Advantageously, in the embodiments mentioned above $R_1$ represents pyridin-2-yl, pyridin-3-yl or pyridin-4-yl, or $R_1$ represents pyrimidin-2-yl or pyrimidin-5-yl.

In particular, 6-membered heteroaryl mentioned above is pyridinyl, especially pyridin-2-yl, pyridin-3-yl or pyridin-4-yl, substituted with C1-C3-alkoxyl, especially with methoxyl or ethoxyl.

In particular, 6-membered heteroaryl mentioned above is pyridinyl, especially pyridin-2-yl, pyridin-3-yl or pyridin-4-yl, substituted with methoxyl.

In particular, 6-membered heteroaryl mentioned above is pyrimidinyl, especially pyrimidin-2-yl or pyrimidin-5-yl, substituted with C1-C3-alkoxyl, especially with methoxyl or ethoxyl.

Definitions

The term "alkyl" as used herein, alone or as a part of another substituent, relates to a hydrocarbon group having straight or branched chain, linked with single carbon-carbon bonds, and having the number of carbon atoms indicated in the definition, for example C1-C4 or C1-C3. The number given after carbon atom relates to the number of carbon atoms that may be comprised in the group. Thus, for example, C1-C4-alkyl means alkyl having 1 to 4 carbon atoms, and C1-C3 alkyl means alkyl having 1 to 3 carbon atoms. C1-C3 alkyl groups are methyl, ethyl, n-propyl, and iso-propyl, and C1-C4 alkyl groups are methyl, ethyl, n-propyl, isopropyl, n-butyl, isobutyl, sec-butyl, and tert-butyl.

The term "heterocyclyl" as used herein relates to a substituent deriving from heterocyclic group, that is alicyclic saturated hydrocarbon group having indicated number of ring members and indicated number and type of heteroatoms.

"Heterocyclyl" includes 6-membered saturated heterocyclic rings comprising 1 or 2 heteroatoms selected from oxygen (O) and nitrogen (N), such as morpholinyl, piperidinyl, piperazinyl, tetrahydropyranyl and dioxanyl, in particular piperidinyl, morpholinyl and pyrrolidinyl.

The term "heteroaryl" as used herein relates to a substituent deriving from heteroaryl group, that is aromatic hydrocarbon cyclic group having indicated number of ring members and indicated number and type of heteroatoms. 6-Membered heteroaryls include in particular pyridinyl, pyridazinyl, pyrimidynyl and pyrazinyl, especially pyridinyl and pyrimidynyl.

Halogen relates to fluorine (F), chlorine (Cl), bromine (Br) or iodine (I) atoms, especially fluorine atom.

Acid addition salts of the compounds of the formula (I) of the invention encompasses in particular salts with pharmaceutically acceptable inorganic or organic acids. Pharmaceutically acceptable salts are the preferred ones. Inorganic and organic acids that may form pharmaceutically acceptable salts with the compounds comprising basic nitrogen atom are well known in the art. Salts with inorganic acids include in particular salts of hydrochloric acid, hydrobromic acid, sulfuric(VI) acid, nitric(V) acid, and phosphoric(V) acid. Salts with organic acids include in particular salts of methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid. It should be understood that the invention includes in its scope also salts other than pharmaceutically acceptable ones useful especially as intermediates in the processes of preparation, isolation and purification of the compounds of the invention.

Acid addition salts can be prepared in a manner commonly known as such. Typically, a compound of the formula (I), for example in a solution in an organic solvent, are reacted with an acid in an aqueous or aqueous-alcoholic solution, such as aqueous methanolic or ethanolic solution, and precipitated salt is isolated in a conventional manner, for example by filtration, washing and drying.

Particular compounds of the invention are selected from the group of the following compounds and their acid addition salts, including inorganic and organic acid addition salts:

1) (R)-7-((1-(6-Cyanopyridazin-3-yl)-3,3-dimethylpiperidin-4-yl)amino)-2-(4-methoxyphenyl)pyrazolo[1,5-a]pyrimidine-6-carboxamide;
2) (R)-7-((1-(6-Cyanopyridazin-3-yl)-3,3-dimethylpiperidin-4-yl)amino)-2-(2-fluoro-5-methoxyphenyl)pyrazolo[1,5-a]pyrimidine-6-carboxamide;
3) (R)-7-((1-(6-Cyanopyridazin-3-yl)-3,3-dimethylpiperidin-4-yl)amino)-2-(pyridin-3-yl)pyrazolo[1,5-a]pyrimidine-6-carboxamide;
4) (R)-7-((1-(6-Cyanopyridazin-3-yl)-3,3-dimethylpiperidin-4-yl)amino)-2-(6-methoxypyridin-3-yl)pyrazolo[1,5-a]pyrimidine-6-carboxamide;
5) (R)-7-((1-(6-Cyanopyridazin-3-yl)-3,3-dimethylpiperidin-4-yl)amino)-2-(6-ethoxypyridin-3-yl)pyrazolo[1,5-a]pyrimidine-6-carboxamide;
6) (R)-2-(6-Aminopyridin-3-yl)-7-((1-(6-cyanopyridazin-3-yl)-3,3-dimethylpiperidin-4-yl)amino)pyrazolo[1,5-a]pyrimidine-6-carboxamide;
7) (R)-7-((1-(6-Cyanopyridazin-3-yl)-3,3-dimethylpiperidin-4-yl)amino)-2-(6-morpholinopyridin-3-yl)pyrazolo[1,5-a]pyrimidine-6-carboxamide;
8) (R)-7-((1-(6-Cyanopyridazin-3-yl)-3,3-dimethylpiperidin-4-yl)amino)-2-(2-methoxypyrimidin-5-yl)pyrazolo[1,5-a]pyrimidine-6-carboxamide;
9) (R)-7-((1-(6-Cyanopyridazin-3-yl)-3,3-dimethylpiperidin-4-yl)amino)-2-(2-ethoxypyrimidin-5-yl)pyrazolo[1,5-a]pyrimidine-6-carboxamide;
10) (R)-7-((1-(6-Cyanopyridazin-3-yl)-3,3-dimethylpiperidin-4-yl)amino)-2-(6-fluoropyridin-3-yl)pyrazolo[1,5-a]pyrimidine-6-carboxamide;
11) (R)-7-((1-(6-Cyanopyridazin-3-yl)-3,3-dimethylpiperidin-4-yl)amino)-2-(6-methoxypyridin-2-yl)pyrazolo[1,5-a]pyrimidine-6-carboxamide;
12) (R)-7-((1-(6-Cyanopyridazin-3-yl)-3,3-dimethylpiperidin-4-yl)amino)-2-(2-methylpyridin-4-yl)pyrazolo[1,5-a]pyrimidine-6-carboxamide;
13) (R)-7-((1-(6-Cyanopyridazin-3-yl)-3,3-dimethylpiperidin-4-yl)amino)-2-(2-morpholinopyridin-4-yl)pyrazolo[1,5-a]pyrimidine-6-carboxamide;
14) (R)-7-((1-(6-Cyanopyridazin-3-yl)-3,3-dimethylpiperidin-4-yl)amino)-2-(6-methoxypyridin-2-yl)pyrazolo[1,5-a]pyrimidine-6-carboxamide hydrochloride.

In a further aspect the invention relates to the compound of the formula (A) as defined above and according to any one presented embodiments for use as a medicament.

In a further aspect the invention relates to a pharmaceutical composition comprising the compound of the formula (A) as defined above and according to any one presented embodiments as the active ingredient, in combination with pharmaceutical excipients.

As kinase JAK1/JAK3 inhibitor, the compounds of the formula (A) as defined above can be useful for the treatment of chronic inflammatory and autoimmunological diseases.

The invention relates therefore to the compound of the formula (I) as defined above for use in a method of treatment of chronic inflammatory and autoimmunological diseases in mammals, including humans.

The invention relates therefore to the use of the compound of the formula (I) as defined above for the preparation of a medicament for use in a method of treatment of chronic inflammatory and autoimmunological diseases in mammals, including humans.

The invention relates also to a method of treatment of chronic inflammatory and autoimmunological diseases in mammals, including humans, which comprises administering to said mammal a therapeutically effective amount of the compound of the formula (I) as defined above or a pharmaceutical composition comprising the compound of the formula (I) as defined above.

Chronic inflammatory and autoimmunological diseases include systemic diseases of a connecting tissue, in particular rheumatoid arthritis, reactive arthritis, psoriatic arthritis, ankylosing spondylitis, systemic lupus erythematosus, scleroderma; non-specific inflammatory bowel diseases, in particular Crohn disease and ulcerative colitis; adrenal glands diseases, in particular multiple sclerosis and myasthenia; skin diseases, in particular psoriasis; and astma.

The compounds of the invention can also find use for prevention of transplant rejection in transplantology.

The compounds of the invention can be prepared by the process presented on Scheme 1.

Below the following abbreviations are used:

AcOEt—ethyl acetate; Boc—tert-butoxycarbonyl group; CN—nitrile group; (COCl)$_2$—oxalyl chloride; Et—ethyl; EtO—ethoxyl; LiOH—lithium hydroxide; Me—methyl; MeCN—acetonitrile; MS-ESI—electrospray mass spectroscopy; m/z—mass to charge ratio; NH$_4$OH—aqueous ammonia, ammonia water; NMR—nuclear magnetic resonance; Pd/C—palladium on carbon; POCl$_3$—phosphorus(V) oxychloride; TFA—trifluoroacetic acid.

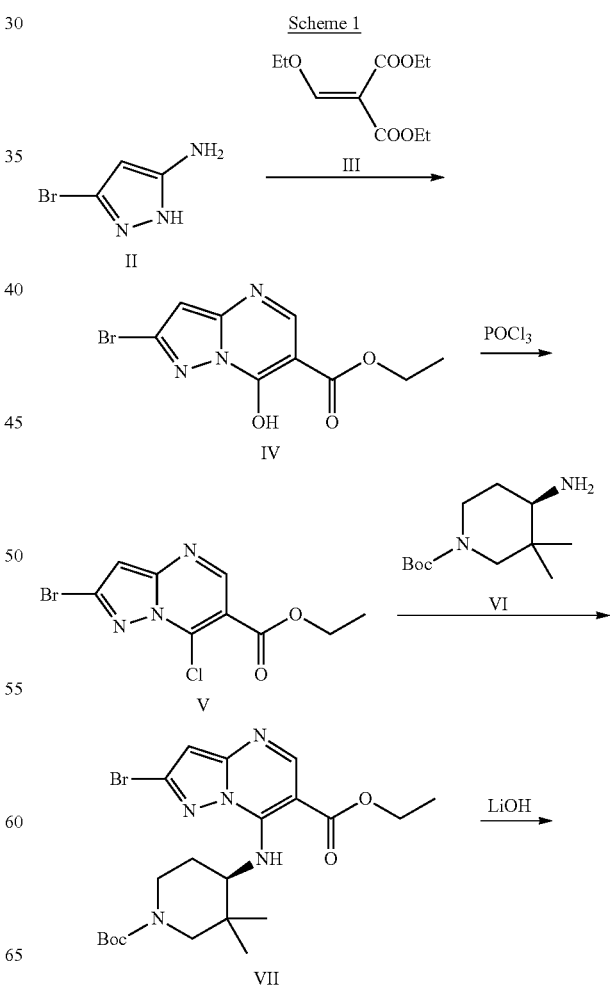

Scheme 1

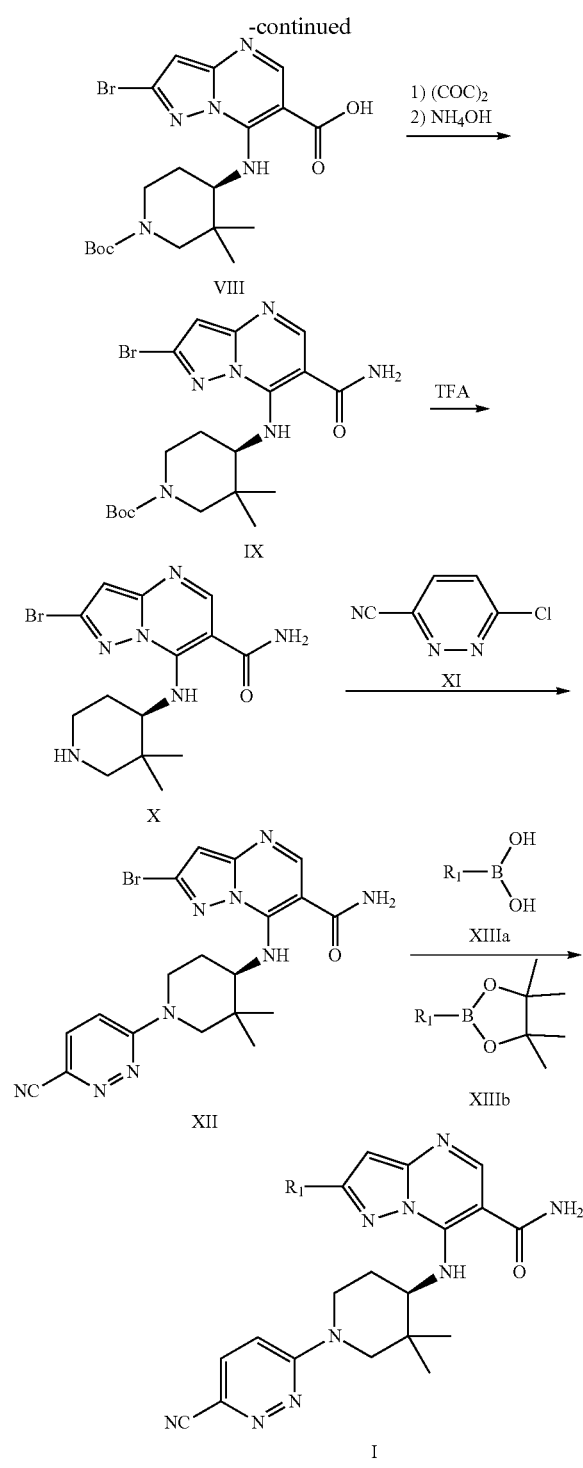

from 2 to 30 molar equivalents, in the presence of an amine such as triethylamine, diisopropyl-ethylamine, pyridine, quinoline, N,N-dimethylaniline, in the amount from 1 to 5 molar equivalents or without amine, with the addition or without a salt such as tetraethylammonium, tetrabutylammonium or benzyltriethylammonium bromide or chloride, in the amount from 1 to 3 molar equivalents, in aprotic solvent such as acetonitrile, tetrahydrofuran, dioxane, toluene, dimethylformamide, methylene chloride, chloroform or without a solvent, at 60 do 120° C. or at reflux.

The compound of the formula V is reacted with tert-butyl (R)-4-amino-3,3-dimethylpiperidine-1-carboxylate VI, obtained in accordance with the procedure described in WO 2014/039595 A1 (Intermediate 4), used in the amount from 1 to 1.5 molar equivalents, in the presence of an amine such as triethylamine, N,N-diisopropylethylamine or pyridine in the amount from 1 to 3 molar equivalents, at 0 to 30° C., to obtain the compound of the formula VII.

Then ester group in the compound of the formula VII is hydrolised to obtain acid VIII using a base such as metal hydroxide, preferably lithium hydroxide, in the amount from 2 to 10 molar equivalents, in a mixture of solvents, such as water/alcohol, preferably water/methanol, at 20 to 80° C., preferably from 40 to 55° C.

Compound of the formula VIII is converted into corresponding amide of the formula IX in a two-step process. In the first step acid chloride is prepared in the reaction with oxalyl chloride in the amount from 2 to 4 molar equivalents, with catalytic amount of dimethylformamide, at 0 to 30° C. Subsequently acid chloride is reacted with aqueous ammonia in the amount from 5 to 20 molar equivalents at 0 to 30° C.

Amine protecting tert-butoxycarbonyl group in the compound of the formula IX is removed using trifluoroacetic acid in the amount 10 to 40 molar equivalents in dichloromethane solution at 0 to 30° C., to obtain the compound of the formula X.

Then compound of the formula X is arylated using 6-chloropyridazine-3-carbonitrile in the amount from 1 to 1.5 molar equivalents in the presence of an amine such as triethylamine, N,N-diisopropylethylamine or pyridine in the amount from 2 to 10 molar equivalents, in aprotic solvent such as dimethylformamide or dichloromethane or protic solvent such as methanol or ethanol, to obtain the compound of the formula XI.

In the last step the compound of the formula XI is reacted in a Suzuki coupling reaction with correspodning boronic acid XIIa or boronic acid pinacol ester of the formula XIIb in the amount from 1 to 2 molar equivalents, in the presence of a palladium catalyst, such as palladium(II) acetate, bis (dibenzylideneacetone)-palladium(0), [1,1'-bis(diphenylphosphine)ferrocene]palladium (II) dichloride dichloromethane adduct, or other conventional Suzuki reaction catalyst in the amount from 0.05 to 0.2 molar equivalents, with the addition of an inorganic base, such as sodium, potassium or cesium carbonate, sodium or potassium phosphate, lithium, sodium or potassium hydroxide, or organic base such as sodium or potassium tert-butanolate, in the amount from 1 to 3 molar equivalents, used as a solid or as an aqueous solution, in a solvent such as toluene, xylene, tetrahydrofuran, dioxane, ethanol, aliphatic alcohols C3 to C6, dimethylformamide or dimethoxyethane, at 80 to 140° C., preferably at reflux temperature.

Compound of the formula VI (tert-butyl (R)-4-amino-3,3-dimethylpiperidine-1-carboxylate) can be obtained according to the procedures described in US2005/182095A1 and WO2014/039595 A1, in accordance with Scheme 3.

As shown on Scheme 1, the compounds of the formula (I) are prepared starting from 5-amino-3-bromo-1H-pyrazole of the formula II.

The compound of the formula II is cyclised with diethyl 2-(ethoxy-methylene)malonate III used in the amount of 1 to 2 molar equivalents, in acetic acid at reflux temperature, to obtain pyrazolo[1,2-b]pyrimidine of the formula IV.

Hydroxy group in the compound of the formula IV is substituted with chlorine using such reagents as phosphorus (V) oxychloride, phosphorus pentachloride, thionyl chloride, preferably phosphorus (V) oxychloride, in the amount Compound of the formula VI can be obtained from commercially available tert-butyl 4-oxopiperidine-1-carboxylate XVIII in the reaction with methylating agent, such as iodomethane, used in the amount from 2 to 3 molar equivalents in the presence of a base, such as sodium hydride, sodium methanolate, sodium tert-butanolate, n-butyllithium, potassium carbonate, preferably sodium hydride, used in the amount from 2 to 3 molar equivalents in an aprotic solvent, such as tetrahydrofuran, toluene, dichloromethane, acetonitrile, preferably tetrahydrofuran, to obtain tert-butyl 3,3-dimethyl-4-oxopiperidine-1-carboxylate XIX.

In the next step, the compound of the formula XIX is converted in a two-step reductive amination reaction.

First, the compound of the formula XIX is reacted with (R)-1-phenylethane-1-amine XX used in the amount from 1 to 2 molar equivalents, optionally in the presence of an acid such as para-toluenesulphonic, benzenesulphonic or sulphuric acid, preferably para-toluenesulphonic acid, used in the amount from 0.05 to 1 molar equivalent in an aprotic solvent such as toluene, benzene or xylene, preferably toluene, at reflux temperature in a reactor with Dean-Stark trap for azeotropic distillation, to obtain tert-butyl (R)-3,3-dimethyl-4-((1-phenylethyl)imino)piperidine-1-carboxylate of the formula XXI, which is used for further reaction without separation.

Then, the reaction mixture with the compound of the formula XXI is cooled to the temperature from −78 to 0° C. and alcohol, such as methanol, ethanol, isopropanol, preferably ethanol, and reducing agent, such as sodium borohydride, sodium cyanoborohydride or sodium triacetoxyborohydride, are added in the amount from 2 to 3 molar equivalents, to obtain tert-butyl (R)-3,3-dimethyl-4-(((R)-1-phenylethyl)amino)piperidine-1-carboxylate of the formula XXII.

In the last step, 1-phenylethyl group protecting amine group in the compound of the formula XXII is removed. 1-Phenylethyl group is removed by reduction using hydrogen and Pd/C catalyst, used in the amount from 0.01 to 0.02 molar equivalents, in a solvent such as methanol, ethanol, iso-propanol, preferably ethanol, to obtain compound of the formula VI, i.e. tert-butyl ((R)-4-amino-3,3-dimethylpiperidine-1-carboxylate.

The compound of the formula II (5-amino-3-bromo-1H-pyrazole) is commercially available. Can be also obtained by a method presented on Scheme 2 from 1H-pyrazole XIV using procedures described in *J. Org. Chem.* 1986, 51, 4656-4660 and *J. Med. Chem.* 2010, 53, 1238-1249.

Scheme 2

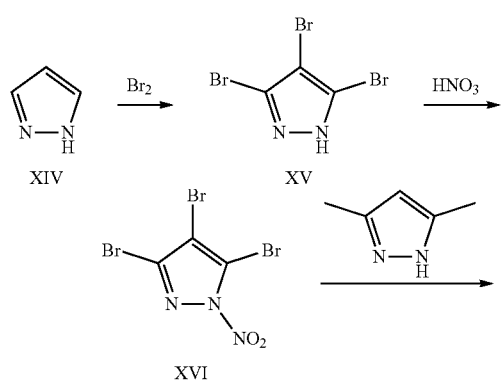

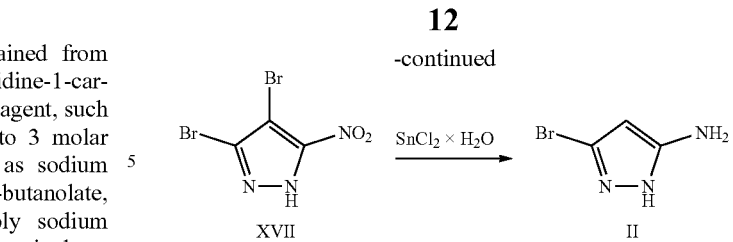

Scheme 3

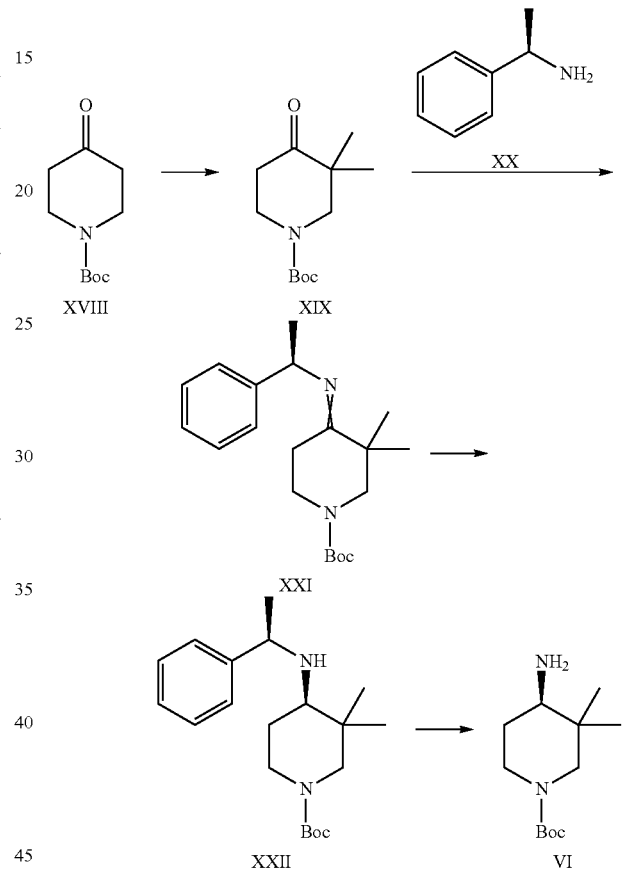

The invention provides also a pharmaceutical composition comprising the compound of the formula (I) as defined above as the active ingredient, in a mixture with pharmaceutically acceptable excipients.

In the treatment of diseases and disorders mentioned above the compounds of the formula (I) of the invention can be administered as a chemical compound, however usually will be used in the form of a pharmaceutical composition comprising the compound of the invention or its pharmaceutically acceptable salt in combination with pharmaceutically acceptable carrier(s) and auxiliary substance(s).

In the treatment of diseases and disorders mentioned above the pharmaceutical composition of the invention can be administered by any suitable route, preferably oral, parenteral or inhalation route and will be in the form of a preparation destined for use in medicine, depending on the intended administration route.

Compositions for oral administration can have the form of solid or liquid preparations. Solid preparations can have, for example, the form of a tablet or capsule produced in a conventional manner from pharmaceutically acceptable inactive excipients such as binders (for example, pregelatinised corn starch, polyvinylpyrrolidone or hydroxypropylmethylcellulose); fillers (for example lactose, saccha rose, carboxymethylcellulose, microcrystalline cellulose or calcium hydrogenphosphate); disintegrants (for example crosspovidone, corn starch or sodium starch glycolate); lubricants (for example magnesium stearate, talc or silica), wetting agents (for example sodium laurylsulphate). Tablets can be coated with coatings well known in the art, such as simple coatings, delayed/controlled-release coatings or enteric coatings. Liquid preparations for oral administration can be in a form of, for example, solutions, syrups or suspensions, or can have the form of dry solid product for reconstitution in water or other suitable vehicle before use. Such liquid preparations can be prepared using conventional means from pharmaceutically acceptable inactive excipients, such as suspending agents (for example sorbitol syrup, cellulose derivatives or hydrogenated edible oils), emulsifiers (for example lecithine or acacia gum), nonaqueous vehicles (for example mandelic oil, oil esters, ethyl alcohol or fractionated vegetable oils), and preservatives (for example methyl or propyl p-hydroxybenzoate or sorbic acid). Preparations can also include suitable buffering agents, flavoring agents, coloring agents and sweeteners.

Preparations for oral administration can be formulated so as to obtain controlled release of the active compound using methods known for a person skilled in the art.

Parenteral route of administration includes administration by intramuscular and intravenous injections, as well as intravenous infusions. Compositions for parenteral administration can, for example, have the form of a unit dosage form, such as ampoules, or multi-dosage containers, with the addition of a preservative. Compositions can have the form such as suspension, solution or emulsion in an oily or aqueous vehicle, and can include excipients such as suspending agents, stabilizers, and/or dispersing agents. Alternatively, the active ingredient can be formulated as a powder for reconstitution before use in a suitable carrier, for example sterile, pyrogen-free water.

Compositions for administration via inhalation route can have the inhalation form and administered by nebulization. Such preparations include an active compound and auxiliary substance(s) administered as an aerosol, i.e. a system of finely divided small particles of solid or liquid substance suspended in a gas. Auxiliary substances used in nebulization can be for example sodium chloride as an isotonicity agent, inorganic acids and hydroxides as pH regulators and stabilizers, benzalkonium chloride as a preservative, sodium citrate as a buffering agent, polysorbate 80 as a surfactant, ethanol and propylene glycol as a co-solvent, and sulphates (VI) as anti-oxidants. Preparations for administration by inhalation route can have the form of pressure inhalers or dry powder inhalers.

The method of treatment with the use of the compounds of the present invention will comprise administration of a therapeutically effective amount of the compound of the invention, preferably in the form of a pharmaceutical composition, to the subject in need of such treatment.

Proposed dosage of the compounds of the invention is from 0.1 to about 1000 mg per day, in a single dose or in divided doses. It will be apparent for a person skilled in the art that selection of a dosage required for obtaining desirable biological effect will depend on many factors, for example specific compound, the indication, the manner of adminis-tration, the age and condition of a patient and that exact dosage will be ultimately determined by a responsible physician.

EXAMPLES

The examples that follow are for illustrative purposes and present conventional synthetic methods used for synthesis of Intermediates used for the preparation of the compounds of the invention.

Intermediates

Intermediates for the preparation of the compounds of the invention are prepared as described below.

Intermediate P1. Compound VI tert-butyl (R)-4-amino-3,3-dimethylpiperidine-1-carboxylate

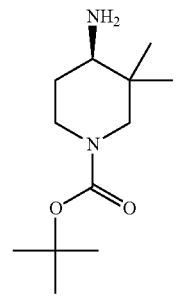 [SMILES: CC(C)(C)OC(=O)N1CC[C@@H](N)C(C)(C)C1]

Step A: Compound XIX—tert-butyl 3,3-dimethyl-4-oxopiperidine-1-carboxylate

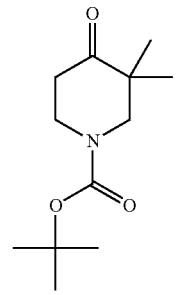 [SMILES: CC(C)(C)OC(=O)N1CCC(=O)C(C)(C)C1]

To the solution of tert-butyl 4-oxopiperidine-1-carboxylate XVIII (50.0 g, 246 mmol) in tetrahydrofuran (1000 mL), cooled to 0° C., sodium hydride (60% suspension in paraffin oil, 21.6 g, 541 mmol) was added portionwise. Reaction mixture was stirred for 2 hours at 0° C. To this mixture iodomethane (34 mL, 541 mmol) solution in tetrahydrofuran (60 mL) was added dropwise during 15 minutes. Reaction mixture was stirred for further 2 hours at 0° C. Saturated ammonium chloride solution (500 mL) was added to the mixture. The mixture was extracted with ethyl acetate (3×500 mL). Organic phases were combined, washed with brine, dried ($Na_2SO_4$) and evaporated under reduced pressure. The residue was purified with column chromatography (silica gel, eluent:hexane:AcOEt=9:1, v/v). The product was purified by crystallization from hot hexane. The product was obtained as white crystals (39.8 g, 175 mmol), yield 71%. $^1$H NMR (300 MHz, DMSO-d$_6$) δ 3.62 (t, J=6.4 Hz, 1H), 3.39 (s, 1H), 2.42 (t, J=6.4 Hz, 1H), 1.46-1.39 (m, 6H), 0.99 (s, 3H).

Step B: Compound XXII—tert-butyl (R)-3,3-dimethyl-4-(((R)-1-phenylethyl)-amino)piperidine-1-carboxylate

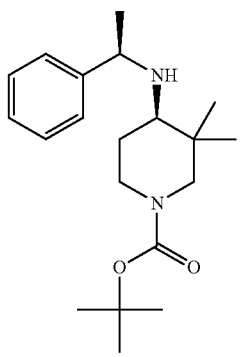 [SMILES: C[C@@H](N[C@@H]1CCN(C(=O)OC(C)(C)C)CC1(C)C)c1ccccc1]

To the solution of tert-butyl 3,3-dimethyl-4-oxopiperidine-1-carboxylate XIX (100 g, 418 mmol) in toluene (1500 mL) (R)-1-phenylethane-1-amine XX (59.7 mL, 460 mmol) and para-toluenesulphonic acid (0.80 g, 4.2 mmol) were added. Reaction mixture was stirred at reflux under azeotropic Dean-Stark trap for 24 hours. Thus obtained mixture containing compound XXI was then cooled to −70° C. without its separation, added with ethanol (100 mL) and sodium borohydride (19.0 g, 502 mmol) was added portionwise. Reaction mixture was stirred for 3 hours while temperature was slowly raised to room temperature. The mixture was added with water (300 mL) and concentrated to ⅓ of its volume. The mixture was extracted with AcOEt (2×300 mL). Organic phases were combined, dried (Na$_2$SO$_4$) and evaporated under reduced pressure. The residue was purified by column chromatography (silica gel, eluent hexane:AcOEt=9:1, v/v). Product was obtained as a colorless oil (67.3 g, 418 mmol) with the yield of 48%. $^1$H NMR (300 MHz, DMSO-d$_6$) δ 7.37-7.25 (m, 4H), 7.22-7.15 (m, 1H), 3.85-3.70 (m, 1H), 3.72 (q, J=6.5 Hz, 1H), 3.58-3.42 (m, 1H), 2.70-2.40 (m, 2H), 2.16 (dd, 1H, J=10.7, 6.51 Hz, 1H), 1.44 (s, 1H), 1.36 (s, 9H), 1.22 (d, J=6.5 Hz, 3H), 1.18-1.02 (m, 1H), 0.92 (s, 3H), 0.76 (s, 3H).

Step C: Compound VI—tert-Butyl (R)-4-amino-3,3-dimethylpiperidine-1-carboxylate

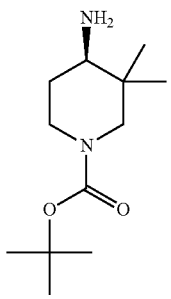 [SMILES: CC(C)(C)OC(=O)N1CC[C@@H](N)C(C)(C)C1]

To a degassed solution of tert-butyl (R)-3,3-dimethyl-4-(((R)-1-phenylethyl)amino)-piperidine-1-carboxylate XXII (44.9 g, 135 mmol) in ethanol (1150 mL) 10% Pd/C (4.0 g) was added. Reaction mixture was stirred at room temperature under hydrogen atmosphere for 20 hours. The mixture was filtered through bed of Celite and concentrated under reduced pressure. The residue was purified by column chromatography (silica gel, eluent:AcOEt to AcOEt:methanol=50:50, v/v). Product was obtained as a colorless oil (26.5 g, 116 mmol) with the yield of 86%. $^1$H NMR (300 MHz, CDCl$_3$) δ 4.20-3.88 (m, 1H), 3.85-3.53 (m, 1H), 2.95-2.70 (m, 1H), 2.60-2.45 (m, 1H), 2.50 (dd, J=10.9, 4.2 Hz, 1H), 1.68-1.54 (m, 1H), 1.45 (s, 9H), 1.45-1.32 (m, 1H), 1.13 (bs, 2H), 0.93 (s, 3H), 0.82 (s, 3H).

Intermediate P2: (R)-2-Bromo-7-((1-(6-cyanopyridazin-3-yl)-3,3-dimethylpiperidin-4-yl)amino)pyrazolo[1,5-a]pyrimidine-6-carboxamide (compound XII)

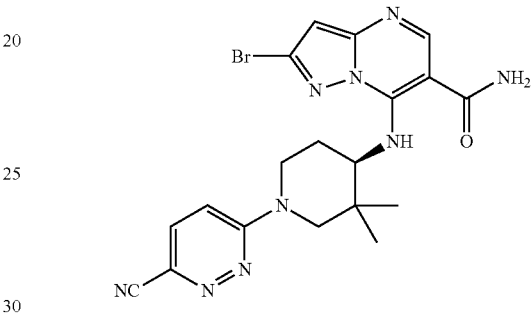

Step 1: Ethyl 2-bromo-7-hydroxypyrazolo[1,5-a]pyrimidine-6-carboxylate IV

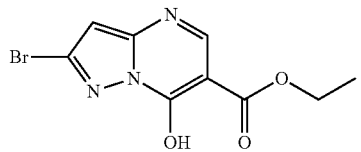 [SMILES: CCOC(=O)c1cnc2cc(Br)nn2c1O]

To the solution of 5-amino-3-bromo-1H-pyrazole II (20.0 g, 121 mmol) in acetic acid (200 mL) diethyl ethoxymethylenemalonate III (25.9 mL, 127 mmol) was added. Reaction mixture was heated at reflux with stirring for 20 hours. Then the mixture was cooled to room temperature, precipitated solid was filtered, washed with ethanol and diethyl ether. Product was obtained as a creamy solid (27.9 g, 97.4 mmol), with the yield 81%. MS-ESI: (m/z) calculated for C$_9$H$_7$BrN$_3$O$_3$[M−H]$^-$=284.0, found 284.0. $^1$H NMR (300 MHz, DMSO-d$_6$) δ 8.37 (s, 1H), 6.15 (s, 1H), 4.50 (bs, 1H), 4.14 (q, J=7.1 Hz, 2H), 1.24 (t, J=7.1 Hz, 3H).

Step 2: Ethyl 2-bromo-7-chloropyrazolo[1,5-a]pyrimidine-6-carboxylate V

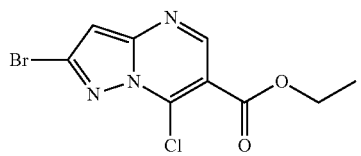 [SMILES: CCOC(=O)c1cnc2cc(Br)nn2c1Cl]

Triethylamine (22.9 mL, 163 mmol) was added to the solution of ethyl 2-bromo-7-hydroxypyrazolo[1,5-a]pyrimidine-6-carboxylate IV (9.34 g, 32.6 mmol) obtained in Step 1 and tetrabutylamonium chloride (18.9 g, 65.3 mmol) in acetonitrile (180 mL). Subsequently phosphorous(V) oxychloride (30.4 mL, 326 mmol) was added dropwise during 15 minutes. Reaction mixture was heated at reflux with stirring for 20 hours. After cooling to room temperature, the reaction mixture was poured to the mixture of saturated sodium carbonate and ice. The mixture was extracted with ethyl acetate (3×300 mL). Organic phases were combined, washed with brine, dried ($Na_2SO_4$) and concentrated under reduced pressure. Residue was purified by column chromatography (silica gel, eluent:heptane:AcOEt=9:1 to 8:2, v/v). Product was obtained as a light-yellow, amorphous solid (6.86 g, 22.5 mmol) with the yield of 69%. MS-ESI: (m/z) calculated for $C_9H_8BrClN_3O_2[M+H]^+$=303.9, found 303.9. $^1$H NMR (300 MHz, $CDCl_3$) δ 8.97 (s, 1H), 6.90 (s, 1H), 4.49 (q, J=7.1 Hz, 2H), 1.46 (t, J=7.1 Hz, 3H).

Step 3: Ethyl (R)-2-bromo-7-((1-(tert-butoxycarbonyl)-3,3-dimethylpiperidin-4-yl)-amino)pyrazolo[1,5-a]pyrimidine-6-carboxylate VII

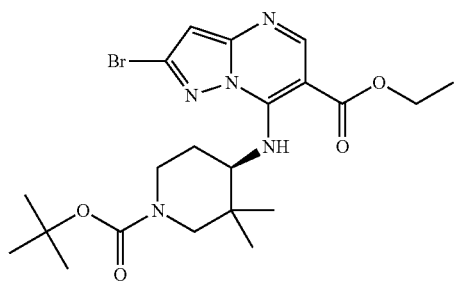 [SMILES: CCOC(=O)c1cnc2cc(Br)nn2c1N[C@@H]1CCN(C(=O)OC(C)(C)C)CC1(C)C]

Triethylamine (8.05 mL, 57.7 mmol) was added to the acetonitrile (150 mL) solution of ethyl 2-bromo-7-chloropyrazolo[1,5-a]pyridimine-6-carboxylate VI (5.86 g, 19.2 mmol) obtained in Step 2. Subsequently, to the mixture solution of tert-butyl (R)-4-amino-3,3-dimethylpiperidine-1-carboxylate VI (Intermediate P1) (4.61 g, 20.2 mmol) in acetonitrile (30 mL) was added dropwise during 15 minutes. Reaction mixture was stirred at room temperature for 20 hours and then concentrated under reduced pressure. The residue was dissolved in AcOEt (100 mL) and water (100 mL) was added. After separation of phases, aqueous phase was extracted with AcOEt (2×100 mL). Organic phases were combined, washed with brine, dried ($Na_2SO_4$) and evaporated under reduced pressure. The residue was purified by column chromatography (silica gel, eluent:heptane:AcOEt=95:5 to 85:15, v/v). Product was obtained as a creamy amorphous solid (8.08 g, 16.3 mmol) with the yield 85%. MS-ESI: (m/z) calculated for $C_{21}H_{31}iBrN_5O_4[M+H]^+$=496.2, found 496.2. $^1$H NMR (300 MHz, $CDCl_3$) δ 9.84 (d, J=8.8 Hz, 1H), 8.70 (s, 1H), 6.47 (s, 1H), 5.32 (t, J=8.6 Hz, 1H), 4.38 (q, J=7.1 Hz, 2H), 4.20-3.95 (m, 1H), 3.93-3.65 (m, 1H), 3.13-2.93 (m, 1H), 2.90-2.70 (m, 1H), 2.08-1.95 (m, 1H), 1.80-1.65 (m, 1H), 1.48 (s, 9H), 1.41 (t, J=7.1 Hz, 3H), 1.09 (s, 3H), 1.00 (s, 3H).

Step 4: (R)-2-Bromo-7-((1-(tert-butoxycarbonyl)-3,3-dimethylpiperidin-4-yl)-amino)pyrazolo[1,5-a]pyrimidine-6-carboxylic acid VIII

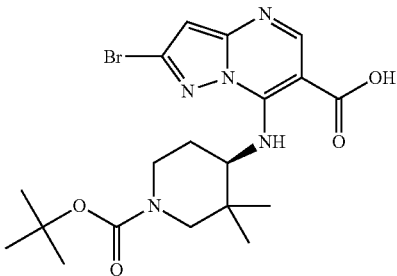 [SMILES: CC(C)(C)OC(=O)N1CC[C@@H](Nc2c(C(=O)O)cnc3cc(Br)nn23)C(C)(C)C1]

To the solution of ethyl (R)-2-bromo-7-((1-(tert-butoxycarbonyl)-3,3-dimethylopiperidin-4-yl)amino)pyrazolo[1,5-a]pyrimidine-6-carboxylate VII (8.06 g, 16.2 mmol) obtained in Step 3 in the mixture of ethanol (200 mL) and water (50 mL) lithium hydroxide (3.41 g, 81.2 mmol) was added. The mixture was heated at 55° C. with stirring for 90 minutes. After cooling to room temperature, ethanol was evaporated from the mixture under reduced pressure. To the residue water (100 mL) was added and subsequently 1M aqueous hydrochloric acid solution until precipitation of white solid. The solid was filtered, washed with water and dried. Then the solid was dissolved in dichloromethane, dried ($Na_2SO_4$) and evaporated under reduced pressure. Raw product obtained as a creamy solid (7.37 g, 15.7 mmol) with the yield of 97% was used in the next step without purification.

Step 5: tert-Butyl (R)-4-((2-bromo-6-carbamoylpyrazolo[1,5-a]pyrimidin-7-yl)-amino)-3,3-dimethylpiperidin-1-carboxylate IX

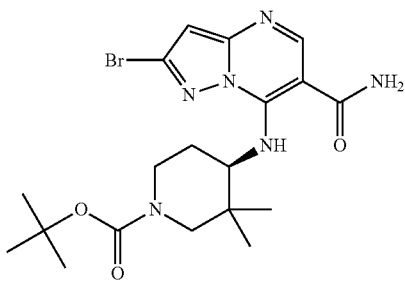 [SMILES: CC(C)(C)OC(=O)N1CC[C@@H](Nc2c(C(N)=O)cnc3cc(Br)nn23)C(C)(C)C1]

Raw (R)-2-bromo-7-((1-(tert-butoxycarbonyl)-3,3-dimethylpiperidin-4-yl)amino)-pyrazolo[1,5-a]pyrimidine-6-carboxylic acid VIII (7.37 g, 15.7 mmol) from Step 4 was dissolved in dry dichloromethane (200 mL) under argon atmosphere. After cooling the mixture was cooled to 0° C., oxalyl chloride (2.72 mL, 31.5 mmol) was added. Then the drop of dimethylformamide (0.5 mL) was added. Reaction mixture was stirred for 30 minutes at room temperature. Subsequently reaction mixture was evaporated under reduced pressure. The residue was dissolved in dry dichloromethane (200 mL). To the mixture 25% aqueous ammonia (24.2 mL, 157 mmol) was added. Reaction mixture was stirred for 30 minutes at room temperature, and dichloromethane was evaporated under reduced pressure. To the residue water (200 mL) was added. The mixture was extracted with AcOEt (3×200 mL). Organic phases were combined, dried (Na$_2$SO$_4$), and evaporated under reduced pressure. The residue was purified by column chromatography (silica gel, eluent:dichloromethane:methanol=97:3, v/v). Product was obtained as white crystals (5.21 g, 11.1 mmol) with the yield 71%. MS-ESI: (m/z) calculated for C$_{19}$H$_{28}$BrN$_6$O$_3$[M+H]$^+$=467.1, found 467.1. $^1$H NMR (300 MHz, CDCl$_3$) δ 10.72 (d, J=9.0 Hz, 1H), 8.35 (s, 1H), 6.45 (s, 1H), 6.04 (bs, 2H), 5.27 (t, J=8.4 Hz, 1H), 4.20-3.93 (m, 1H), 3.90-3.63 (m, 1H), 3.15-2.90 (m, 1H), 2.90-2.67 (m, 1H), 2.02 (dq, J=7.3, 3.4 Hz, 1H), 1.80-1.65 (m, 1H), 1.47 (s, 9H), 1.08 (s, 3H), 0.99 (s, 3H).

Step 6: (R)-2-Bromo-7-((3,3-dimethylpiperidin-4-yl)amino)pyrazolo[1,5-a]-pyrimidine-6-carboxamide X

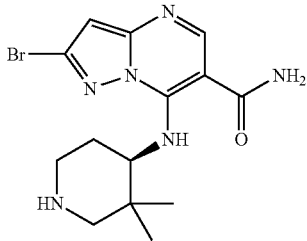 [SMILES: CC1(C)CNCC[C@H]1Nc1c(C(N)=O)cnc2cc(Br)nn12]

To the solution of tert-butyl (R)-4-((2-bromo-6-carbamoylpyrazolo[1,5-a]pyrimidin-7-yl)amino)-3,3-dimethylpiperidine-1-carboxylate IX (5.21 g, 11.1 mmol) from Step 5 in dichloromethane (80 mL), trifluoroacetic acid (8.53 mL, 111 mmol) was added. Reaction mixture was stirred at room temperature for 1 hour. Volatiles were evaporated under reduced pressure. To the residue water (100 mL) was added, and then 6 M sodium hydroxide until pH=12. White solid precipitated from the mixture. Mixture was extracted with AcOEt (3×100 mL). Organic phases were combined, dried (Na$_2$SO$_4$), and evaporated. Raw product obtained as a white solid (4.09 g, 11.1 mmol) with the yield 100% was used in the next step without further purification.

Step 7: (R)-2-Bromo-7-((1-(6-cyanopyridazin-3-yl)-3,3-dimethylpiperidin-4-yl)-amino)pyrazolo[1,5-a]pyrimidine-6-carboxamide XII

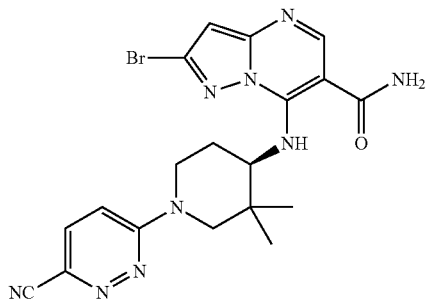 [SMILES: CC1(C)CN(c2ccc(C#N)nn2)CC[C@H]1Nc1c(C(N)=O)cnc2cc(Br)nn12]

Raw (R)-2-bromo-7-((3,3-dimethylpiperidin-4-yl)amino)pyrazolo[1,5-a]pyrimidine-6-carboxamide XI (2.05 g, 5.58 mmol) from Step 6 was dissolved in dry dimethylformamide (50 mL) under argon atmosphere. To the solution triethylamine (3.91 mL, 27.9 mmol) and then 6-chloropyridazine-3-carbonitrile (963 mg, 6.69 mmol) were added. Reaction mixture was heated at 80° C. with stirring for 1 hour. After cooling to room temperature, 100 mL of water was added and the mixture was extracted with AcOEt (3×100 mL). Organic phases were combined, dried and evaporated under reduced pressure. To the residue toluene (50 mL) was added and evaporated under reduced pressure. This was repeated twice. The residue was purified by column chromatography (silica gel, eluent:dichloromethane:methanol=98:2, v/v). Product was obtained as a light-yellow solid (2.35 g, 4.99 mmol) with the yield of 89%. MS-ESI: (m/z) calculated for C$_{19}$H$_{21}$BrN$_9$O [M+H]$^+$=470.1, found 470.1. $^1$H NMR (300 MHz, CDCl$_3$) δ 11.06 (d, J=8.3 Hz, 1H), 8.44 (s, 1H), 7.50 (d, J=9.7 Hz, 1H), 6.99 (d, J=9.7 Hz, 1H), 6.45 (s, 1H), 6.04 (bs, 2H), 5.49 (dd, J=10.6, 4.2 Hz, 1H), 4.48 (d, J=13.3 Hz, 1H), 4.29 (d, J=13.6 Hz, 1H), 3.40 (ddd, J=13.6, 9.4, 3.3 Hz, 1H), 3.17 (d, J=13.7 Hz, 1H), 2.26 (dq, J=11.3, 3.6 Hz, 1H), 1.96-1.80 (m, 1H), 1.11 (s, 3H), 1.10 (s, 3H).

Compounds of the invention were prepared from Intermediate P2 and respective boronic acid XIIa or boronic acid pinacol ester XIIb, in accordance with the general procedure, as described in the following examples.

General procedure: To the mixture of (R)-2-bromo-7-((1-(6-cyanopyridazin-3-yl)-3,3-dimethylpiperidin-4-yl)amino)pyrazolo[1,5-a]pyrimidine-6-carboxamide (Intermediate P2) (1 eq.), [1,1'-bis(diphenylphosphino)ferrocene]dichloropalladium(II) dichloromethane complex (0.1 eq.) and respective boronic acid (2 eq) or boronic acid pinacol ester in degassed dioxane (20 mL/1 mmol P2) in a Schlenk flask degassed 2 M aqueous potassium phosphate (3 eq.) solution was added. Through the reaction mixture argon was purged for 15 minutes. The flask was tightly closed and the reaction mixture was heated to 120° C. with stirring for 3 hours. Then the reaction mixture was cooled, diluted with ethyl acetate, filtered through bed of Celite and concentrated under reduced pressure. The oily residue was purified by column chromatography (silica gel: eluent: hexane:AcOEt) to obtain a product.

Example 1

(R)-7-((1-(6-Cyanopyridazin-3-yl)-3,3-dimethylpiperidin-4-yl)amino)-2-(4-methoxy-phenyl)pyrazolo[1,5-a]pyrimidine-6-carboxamide

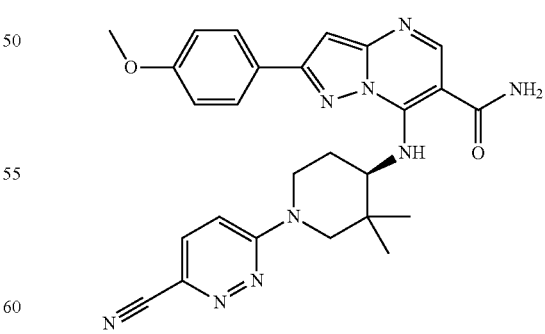

Prepared using Compound P2 (51 mg, 0.11 mmol) and (4-methoxyphenyl)boronic acid (33, mg, 0.22 mmol) as a white amorphous solid (29 mg, 0.058 mmol), with the yield 53%. MS-ESI: (m/z) calculated for C$_{26}$H$_{28}$N$_9$O$_2$[M+H]$^+$=498.2, found 498.2.$^1$H NMR (300 MHz, CD$_3$OD) δ

8.51 (s, 1H), 7.92 (d, J=8.7 Hz, 2H), 7.66 (d, J=9.7 Hz, 1H), 7.67-7.47 (m, 2H), 7.35 (d, J=9.9 Hz, 1H), 7.03 (d, J=8.6 Hz, 2H), 6.71 (s, 1H), 5.82-5.70 (m, 1H), 4.67-4.55 (m, 1H), 4.42-4.25 (m, 1H), 3.85 (s, 3H), 3.50-3.38 (m, 1H), 3.21 (d, J=14.3 Hz, 1H), 2.42-2.27 (m, 1H), 2.05-1.85 (m, 1H), 1.12 (s, 6H).

Example 2

(R)-7-((1-(6-Cyanopyridazin-3-yl)-3,3-dimethylpiperidin-4-yl)amino)-2-(2-fluoro-5-methoxyphenyl)pyrazolo[

1,5-a]pyrimidine-6-carboxamide

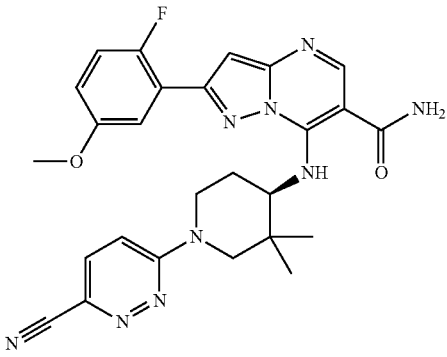 [SMILES: COc1ccc(F)c(-c2cc3ncc(C(N)=O)c(N[C@@H]4CCN(c5ccc(C#N)nn5)CC4(C)C)n3n2)c1]

Prepared from Compound P2 (47 mg, 0.10 mmol) and (2-fluoro-5-methoxy-phenyl)boronic acid (34 mg, 0.20 mmol) as a white amorphous solid (25 mg, 0.049 mmol) with the yield of 49%. MS-ESI: (m/z) calculated for $C_{26}H_{27}FN_9O_2[M+H]^+=516.2$, found 516.2. $^1$H NMR (300 MHz, DMSO-$d_6$) δ 11.22 (bs, 1H), 8.67 (s, 1H), 8.19 (bs, 1H), 7.87 (d, J=9.7 Hz, 1H), 7.59 (dd, J=5.8, 3.2 Hz, 1H), 7.55 (bs, 1H), 7.49 (d, J=9.8 Hz, 1H), 7.33 (dd, J=10.6, 9.2 Hz, 1H), 7.06 (dt, J=9.0, 3.5 Hz, 1H), 6.88 (d, J=3.3 Hz, 1H), 5.58-5.46 (m, 1H), 4.68 (d, J=13.7 Hz, 1H), 4.33 (d, J=13.5 Hz, 1H), 3.85 (s, 3H), 3.34-3.24 (m, 1H), 3.13 (d, J=13.7 Hz, 1H), 2.36-2.24 (m, 1H), 1.92-1.74 (m, 1H), 1.05 (s, 3H), 1.04 (s, 3H).

Example 3

(R)-7-((1-(6-Cyanopyridazin-3-yl)-3,3-dimethylpiperidin-4-yl)amino)-2-(pyridin-3-yl)pyrazolo[1,5-a]pyrimidine-6-carboxamide

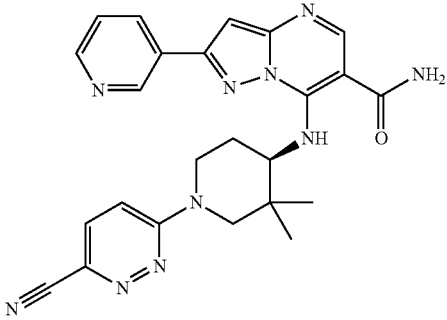 [SMILES: CC1(C)CN(c2ccc(C#N)nn2)CC[C@H]1Nc1c(C(N)=O)cnc2cc(-c3cccnc3)nn12]

Obtained from Compound P2 (50 mg, 0.11 mmol) and 3-(4,4,5,5-tetramethyl-1,3,2-dioxaborolan-2-yl)pyridine (45 mg, 0.22 mmol) as a yellow amorphous solid (40 mg, 0.085 mmol), with the yield 78%. MS-ESI: (m/z) calculated for $C_{24}H_{25}N_{10}O$ [M+H]$^+$=469.2, found 469.2. $^1$H NMR (300 MHz, DMSO-$d_6$) δ 11.23 (d, J=6.2 Hz, 1H), 9.26 (dd, J=2.0, 0.5 Hz, 1H), 8.65 (s, 1H), 8.65 (dd, J=4.7 Hz, 1H), 8.41 (dt, J=8.0, 1.9 Hz, 1H), 8.17 (bs, 1H), 7.87 (d, J=9.7 Hz, 1H), 7.56 (ddd, J=7.9, 4.8, 0.7 Hz, 1H), 7.53 (bs, 1H), 7.49 (d, J=9.8 Hz, 1H), 7.13 (s, 1H), 5.58-5.47 (m, 1H), 4.63 (d, J=12.2 Hz, 1H), 4.33 (d, J=14.0 Hz, 1H), 3.44-3.34 (m, 1H), 3.22 (d, J=13.5 Hz, 1H), 2.32-2.20 (m, 1H), 1.90-1.74 (m, 1H), 1.04 (s, 3H), 1.03 (s, 3H).

Example 4

(R)-7-((1-(6-Cyanopyridazin-3-yl)-3,3-dimethylpiperidin-4-yl)amino)-2-(6-methoxy-pyridin-3-yl)pyrazolo[1,5-a]pyrimidine-6-carboxamide

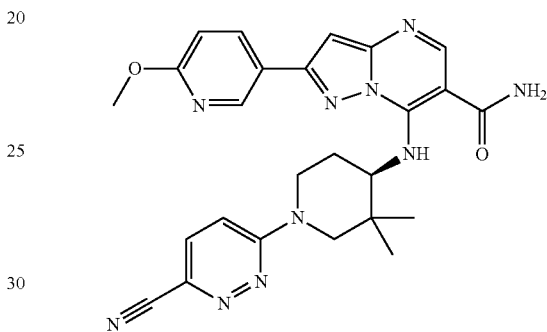

Prepared from Compound P2 (47 mg, 0.10 mmol) and (6-methoxypyridin-3-yl)boronic acid (31 mg, 0.20 mmol) as a white amorphous solid (33 mg, 0.066 mmol), with the yield 66%. MS-ESI: (m/z) calculated from $C_{26}H_{27}N_{10}O_2$ [M+H]$^+$=499.2, found 499.2. $^1$H NMR (300 MHz, DMSO-$d_6$) δ 11.20 (d, J=5.9 Hz, 1H), 8.87 (d, J=1.3 Hz, 1H), 8.63 (s, 1H), 8.32 (dd, J=8.6, 1.7 Hz, 1H), 8.14 (bs, 1H), 7.87 (d, J=9.7 Hz, 1H), 7.50 (bs, 1H), 7.49 (d, J=9.7 Hz, 1H), 7.01 (s, 1H), 6.98 (d, J=8.7 Hz, 1H), 5.58-5.45 (m, 1H), 4.62 (d, J=12.3 Hz, 1H), 4.33 (d, J=13.4 Hz, 1H), 3.92 (s, 3H), 3.44-3.34 (m, 1H), 3.22 (d, J=13.6 Hz, 1H), 2.31-2.19 (m, 1H), 1.90-1.72 (1H), 1.04 (s, 3H), 1.02 (s, 3H).

Example 5

(R)-7-((1-(6-Cyanopyridazin-3-yl)-3,3-dimethylpiperidin-4-yl)amino)-2-(6-ethoxy-pyridin-3-yl)pyrazolo[1,5-a]pyridimine-6-carboxamide

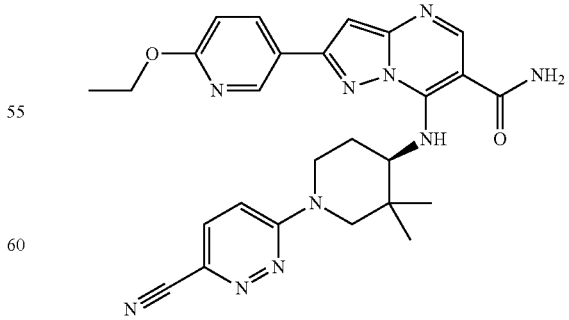

Prepared from Compound P2 (53 mg, 0.11 mmol) and (6-ethoxypyridin-3-yl)boronic acid (37 mg, 0.22 mmol) as a creamy amorphous solid (34 mg, 0.066 mmol), with the yield 60%. MS-ESI: (m/z) calculated for $C_{26}H_{29}N_{10}O_2$[M+

H]⁺=513.2, found 513.2. ¹H NMR (300 MHz, CDCl₃) δ 11.26 (d, J=8.2 Hz, 1H), 8.74 (s, 2H), 8.04 (d, J=8.3 Hz, 1H), 7.46 (d, J=9.5 Hz, 1H), 6.91 (d, J=9.6 Hz, 1H), 6.84 (d, J=8.6 Hz, 1H), 6.77 (s, 1H), 6.21 (bs, 2H), 5.78-5.65 (m, 1H), 4.53 (d, J=12.9 Hz, 1H), 4.42 (t, J=7.1 Hz, 2H), 4.32 (d, J=13.6 Hz, 1H), 3.44 (t, J=11.5 Hz, 1H), 3.19 (d, J=13.9 Hz, 1H), 2.36 (d, J=11.2 Hz, 1H), 2.06-1.86 (m, 1H), 1.44 (t, J=7.1 Hz, 3H), 1.16 (s, 6H).

Example 6

(R)-2-(6-Aminopyridin-3-yl)-7-((1-(6-cyano-pyridazin-3-yl)-3,3-dimethylpiperidin-4-yl)amino)pyrazolo[1,5-a]pyrimidine-6-carboxamide

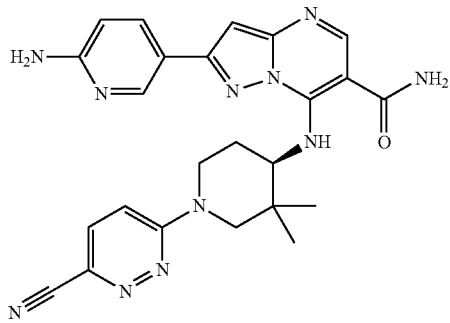 [SMILES: CC1(C)CN(c2ccc(C#N)nn2)CC[C@H]1Nc1c(C(N)=O)cnc2cc(-c3ccc(N)nc3)nn12]

Prepared from Compound P2 (48 mg, 0.10 mmol) and 5-(4,4,5,5-tetramethyl-1,3,2-dioxaborolan-2-yl)pyridin-2-amine (44 mg, 0.20 mmol) as a white amorphous solid (22 mg, 0.046 mmol) with the yield 46%. MS-ESI: (m/z) calculated for $C_{24}H_{26}N_{11}O$ [M+H]⁺=484.2, found 484.2. ¹H NMR (300 MHz, CDCl₃) δ 11.03-10.91 (m, 1H), 8.56 (dd, J=2.3, 0.7 Hz, 1H), 8.40 (s, 1H), 8.08 (dd, J=2.4, 0.7 Hz, 1H), 7.96 (dd, J=8.7, 2.3 Hz, 1H), 7.63 (dd, J=8.7, 2.5 Hz, 1H), 7.49 (d, J=9.6 Hz, 1H), 6.98 (d, J=9.7 Hz, 1H), 6.66 (ddd, J=8.7, 2.1, 0.7 Hz, 2H), 6.62 (s, 1H), 5.67 (dd, J=10.3, 3.8 Hz, 1H), 4.53 (d, J=13.7 Hz, 1H), 4.30 (d, J=13.1 Hz, 1H), 3.48-3.35 (m, 2H), 2.42-2.30 (m, 1H), 2.03-1.86 (m, 1H), 1.14 (s, 6H).

Example 7

(R)-7-((1-(6-Cyanopyridazin-3-yl)-3,3-dimethylpiperidin-4-yl)amino)-2-(6-morpholinopyridin-3-yl)pyrazolo[1,5-a]pyrimidine-6-carboxamide

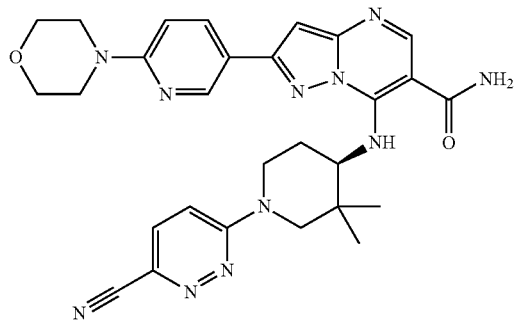 [SMILES: CC1(C)CN(c2ccc(C#N)nn2)CC[C@H]1Nc1c(C(N)=O)cnc2cc(-c3ccc(N4CCOCC4)nc3)nn12]

Prepared from Compound P2 (51 mg, 0.11 mmol) and 4-(5-(4,4,5,5-tetramethyl-1,3,2-dioxaborolan-2-yl)pirydyn-2-yl)morpholine (58 mg, 0.20 mmol) as a creamy amoprhous solid (20 mg, 0.036 mmol) with the yield 33%. MS-ESI: (m/z) calculated for $C_{28}H_{32}N_{11}O_2$[M+H]⁺=554.3, found 554.2. ¹H NMR (300 MHz, CDCl₃) δ 10.87 (d, J=8.8 Hz, 1H), 8.78 (d, J=2.1 Hz, 1H), 8.42 (s, 1H), 7.97 (dd, J=8.9, 2.4 Hz, 1H), 7.44 (d, J=9.6 Hz, 1H), 6.90 (d, J=9.7 Hz, 1H), 6.73 (d, J=8.8 Hz, 1H), 6.67 (s, 1H), 5.94 (bs, 2H), 5.71 (ddd, J=10.3, 8.9, 4.2 Hz, 1H), 4.52 (d, J=13.3 Hz, 1H), 4.29 (d, J=13.5 Hz, 1H), 3.88-3.82 (m, 4H), 3.64-3.57 (m, 4H), 3.49-3.37 (m, 1H), 3.17 (d, J=13.7 Hz, 1H), 2.42-2.30 (m, 1H), 1.94 (ddd, J=15.2, 11.7, 4.6 Hz, 1H), 1.14 (s, 6H).

Example 8

(R)-7-((1-(6-Cyanopyridazin-3-yl)-3,3-dimethylpiperidin-4-yl)amino)-2-(2-methoxy-pyrimidin-5-yl)pyrazolo[1,5-a]pyrimidine-6-carboxamide

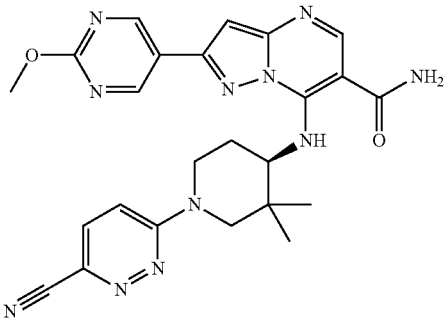 [SMILES: COc1ncc(-c2cc3ncc(C(N)=O)c(N[C@@H]4CCN(c5ccc(C#N)nn5)CC4(C)C)n3n2)cn1]

Prepared from Compound P2 (53 mg, 0.11 mmol) and (2-methoxypyrimidin-5-yl)boronic acid (34 mg, 0.22 mmol) as a white amorphous solid (42 mg, 0.084 mmol) with the yield 76%. MS-ESI: (m/z) calculated for $C_{24}H_{26}N_{11}O_2$[M+H]⁺=500.2, found 500.2. ¹H NMR (300 MHz, CDCl₃) δ 11.18 (d, J=8.1 Hz, 1H), 9.03 (s, 2H), 8.63 (s, 1H), 7.46 (d, J=9.6 Hz, 1H), 6.91 (d, J=9.6 Hz, 1H), 6.80 (s, 1H), 6.13 (bs, 2H), 5.72-5.57 (m, 1H), 4.52 (d, J=12.7 Hz, 1H), 4.33 (d, J=13.7 Hz, 1H), 4.10 (s, 3H), 3.42 (t, J=10.9 Hz, 1H), 3.17 (d, J=13.7 Hz, 1H), 2.42-2.24 (m, 1H), 2.06-1.90 (m, 1H), 1.16 (s, 3H), 1.15 (s, 3H).

Example 9

(R)-7-((1-(6-Cyanopyridazin-3-yl)-3,3-dimethylpiperidin-4-yl)amino)-2-(2-ethoxy-pyrimidin-5-yl)pyrazolo[1,5-a]pyrimidine-6-carboxamide

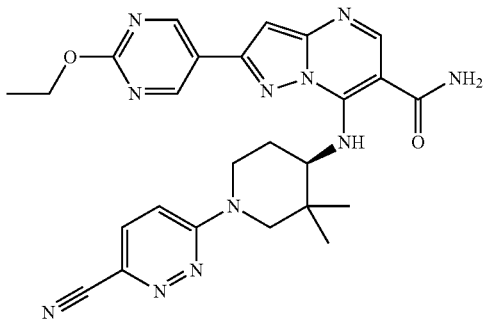 [SMILES: CCOc1ncc(-c2cc3ncc(C(N)=O)c(N[C@@H]4CCN(c5ccc(C#N)nn5)CC4(C)C)n3n2)cn1]

Prepared from Compound P2 (50 mg, 0.11 mmol) and (2-ethoxypyrimidin-5-yl)-boronic acid (37 mg, 0.22 mmol) as a white amorphous solid (17 mg, 0.033 mmol) with the yield 30%. MS-ESI: (m/z) calculated for $C_{25}H_{28}N_{11}O_2[M+H]^+$=514.2, found 514.2. $^1$H NMR (300 MHz, CDCl$_3$) δ 11.07 (d, J=8.8 Hz, 1H), 9.00 (s, 2H), 8.54 (s, 1H), 7.45 (d, J=9.5 Hz, 1H), 6.90 (d, J=9.7 Hz, 1H), 6.76 (s, 1H), 6.04 (bs, 2H), 5.70-5.58 (m, 1H), 4.50 (q, J=7.0 Hz, 3H), 4.32 (d, J=13.6 Hz, 1H), 3.41 (t, J=11.4 Hz, 1H), 3.16 (d, J=13.6 Hz, 1H), 2.34 (d, J=10.5 Hz, 1H), 2.10-1.94 (m, 1H), 1.47 (t, J=7.1 Hz, 3H), 1.15 (s, 3H), 1.14 (s, 3H).

Example 10

(R)-7-((1-(6-Cyanopyridazin-3-yl)-3,3-dimethylpiperidin-4-yl)amino)-2-(6-fluoro-pyridin-3-yl)pyrazolo[1,5-a]pyrimidine-6-carboxamide

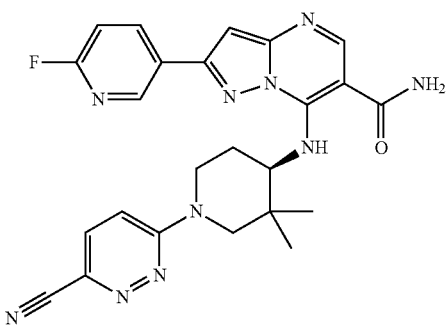 [SMILES: CC1(C)CN(c2ccc(C#N)nn2)CC[C@H]1Nc1c(C(N)=O)cnc2cc(-c3ccc(F)nc3)nn12]

Prepared from Compound P2 (47 mg, 0.10 mmol) and (6-fluoropyridin-3-yl)boronic acid (28 mg, 0.20 mmol) as a creamy, amorphous solid (38 mg, 0.078 mmol) with the yield 78%. MS-ESI: (m/z) calculated for $[M+H]^+$=487.2, found 487.2. $^1$H NMR (300 MHz, CDCl$_3$) δ 11.06 (d, J=8.8 Hz, 1H), 8.79 (d, J=2.4 Hz, 1H), 8.44 (s, 1H), 8.29 (ddd, J=8.3, 7.8, 2.5 Hz, 1H), 7.48 (d, J=9.7 Hz, 1H), 7.09 (dd, J=8.5, 2.8 Hz, 1H), 6.95 (d, J=9.7 Hz, 1H), 6.74 (s, 1H), 5.65 (dd, J=10.4, 4.1 Hz, 1H), 4.52 (d, J=13.3 Hz, 1H), 4.31 (d, J=13.5 Hz, 1H), 3.50-3.34 (m, 1H), 3.18 (d, J=13.8 Hz, 1H), 2.40-2.28 (m, 1H), 2.06-1.88 (m, 1H), 1.15 (s, 6H).

Example 11

(R)-7-((1-(6-Cyanopyridazin-3-yl)-3,3-dimethylpiperidin-4-yl)amino)-2-(6-methoxy-pyridin-2-yl)pyrazolo[1,5-a]pyrimidine-6-carboxamide

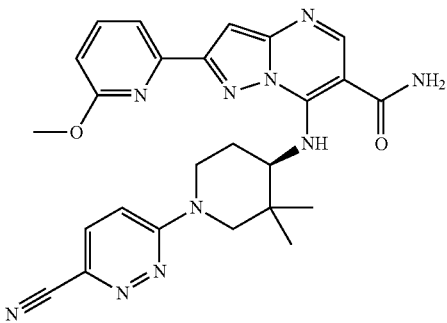

Prepared from Compound P2 (201 mg, 0.43 mmol) and 2-methoxy-6-(4,4,5,5-tetramethyl-1,3,2-dioxaborolan-2-yl)pyridine (202 mg, 0.86 mmol) as a white amorphous solid (144 mg, 0.29 mmol) with the yield 67%. MS-ESI: (m/z) calculated for $C_{26}H_{27}N_{10}O_2[M+H]^+$=499.2, found 499.2. $^1$H NMR (300 MHz, DMSO-d$_6$) δ11.32 (d, J=8.8 Hz, 1H), 8.73 (s, 1H), 8.65 (d, J=5.1 Hz, 1H), 8.24 (s, 1H), 7.94 (d, J=9.8 Hz, 1H), 7.93 (s, 1H), 7.87 (d, J=5.1 Hz, 1H), 7.60 (bs, 1H), 7.57 (d, J=9.8 Hz, 1H), 7.21 (s, 1H), 5.62-5.50 (m, 1H), 4.73 (d, J=11.9 Hz, 1H), 4.42 (d, J=13.5 Hz, 1H), 3.52-3.40 (m, 1H), 3.28 (d, J=13.7 Hz, 1H), 2.64 (s, 3H), 2.35 (d, J=9.7 Hz, 1H), 1.98-1.80 (m, 1H), 1.11 (s, 3H), 1.10 (s, 3H).

Example 12

(R)-7-((1-(6-Cyanopyridazin-3-yl)-3,3-dimethylpiperidin-4-yl)amino)-2-(2-methyl-pyridin-4-yl)pyrazolo[1,5-a]pyrimidine-6-carboxamide

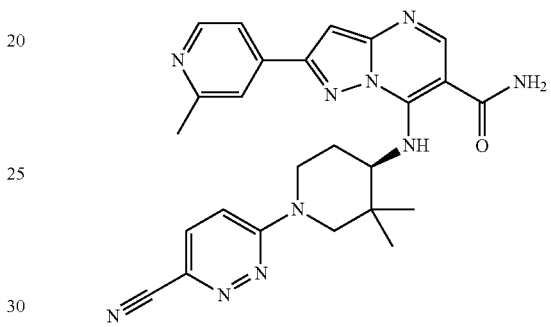

Prepared from Compound P2 (49 mg, 0.10 mmol) and 2-methyl-4-(4,4,5,5-tetramethyl-1,3,2-dioxaborolan-2-yl)pyridine (44, mg, 0.20 mmol) as a white, amorphous solid (20 mg, 0.050 mmol) with the yield 41%. MS-ESI: (m/z) calculated for $C_{26}H_{27}N_{10}O$ $[M+H]^+$=483.2, found 483.2. $^1$H NMR (300 MHz, CDCl$_3$) δ 10.89 (d, J=8.5 Hz, 1H), 8.62 (d, J=5.4 Hz, 1H), 8.36 (s, 1H), 7.66-7.57 (m, 2H), 7.46 (d, J=9.6 Hz, 1H), 6.92 (d, J=9.5 Hz, 1H), 6.85 (s, 1H), 5.86-5.61 (m, 3H), 4.58 (d, J=13.0 Hz, 1H), 4.33 (d, J=13.6 Hz, 1H), 3.44 (t, J=12.3 Hz, 1H), 3.19 (d, J=13.6 Hz, 1H), 2.6 (s, 3H), 2.40 (dd, J=13.4, 3.7 Hz, 1H), 2.07-1.90 (m, 1H), 1.16 (s, 6H).

Example 13

(R)-7-((1-(6-Cyanopyridazin-3-yl)-3,3-dimethylpiperidin-4-yl)amino)-2-(2-morpholinopyridin-4-yl)pyrazolo[1,5-a]pyrimidine-6-carboxamide

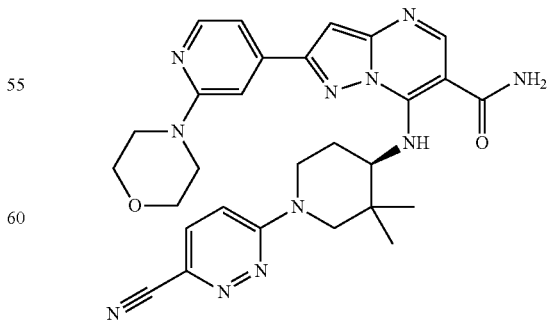

Prepared from Compound P2 (52 mg, 0.11 mmol) and (2-morpholinopyridin-4-yl)-boronic acid (46 mg, 0.22 mmol) as a white amorphous solid (30 mg, 0.054 mmol) with the yield 49%. MS-ESI: (m/z) calculated for $C_{28}H_{32}N_{11}O_2[M+H]^+=554.3$, found 554.2. $^1$H NMR (300 MHz, CDCl$_3$) δ 11.05 (d, J=8.2 Hz, 1H), 8.48 (s, 1H), 8.29 (d, J=5.2 Hz, 1H), 7.49 (d, J=9.6 Hz, 1H), 7.20 (dd, J=5.2, 1.1 Hz, 1H), 7.12 (s, 1H), 6.97 (d, J=9.7 Hz, 1H), 6.78 (s, 1H), 5.68 (dd, J=10.3, 4.0 Hz, 1H), 4.55 (d, J=13.4 Hz, 1H), 4.28 (d, J=13.8 Hz, 1H), 3.91-3.84 (m, 4H), 3.64-3.56 (m, 4H), 3.43-3.31 (m, 1H), 3.18 (d, J=13.7 Hz, 1H), 2.45-2.30 (m, 1H), 2.05-1.89 (m, 1H), 1.15 (s, 6H).

Example 14

(R)-7-((1-(6-Cyanopyridazin-3-yl)-3,3-dimethylpiperidin-4-yl)amino)-2-(6-methoxy-pyridin-2-yl)pyrazolo[1,5-a]pyrimidine-6-carboxamide

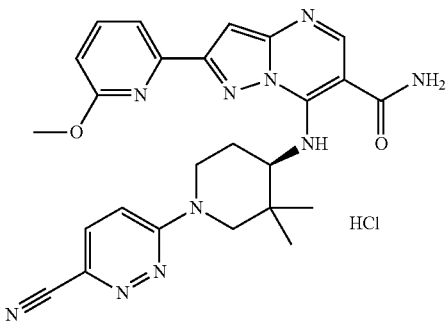 [SMILES: COc1cccc(-c2cc3ncc(C(N)=O)c(N[C@@H]4CCN(c5ccc(C#N)nn5)CC4(C)C)n3n2)n1]

37% Aqueous solution of hydrochloric acid (170 μl, 2.01 mmol, 1.0 eq) was added to the solution of (R)-7-((1-(6-cyanopyridazin-3-yl)-3,3-dimethylpiperidin-4-yl)-amino)-2-(6-methoxypyridin-2-yl)pyrazolo[1,5-a]pyrimidine-6-carboxamide (100 mg, 0.201 mmol) in acetone (10 mL). Precipitated white solid was filtered, washed with acetone, and dried to obtain the product (90 mg, 0.168 mmol) with the yield 84%. $^1$H NMR (300 MHz, DMSO-d$_6$) δ 12.20 (d, J=6.6 Hz, 1H), 9.00 (s, 1H), 8.57 (bs, 1H), 7.95-7.78 (m, 4H), 7.50 (d, J=9.8 Hz, 1H), 7.04 (s, 1H), 6.94 (d, J=9.8 Hz, 1H), 5.70-5.50 (m, 1H), 4.63 (d, J=13.2 Hz, 1H), 4.35 (d, J=13.7 Hz, 1H), 3.98 (s, 3H), 3.39 (t, J=11.3 Hz, 1H), 3.23 (d, J=13.7 Hz, 1H), 2.35-2.22 (m, 1H), 1.95-1.77 (m, 1H), 1.08 (s, 3H), 1.05 (s, 3H).

Biological Activity of the Compounds of the Invention

In Vitro JAK Kinase Inhibition Assay

The effects of the compounds of the invention were analysed in vitro using kinase JAK inhibition assay described below.

Tested compounds were dissolved in 100% DMSO, and obtained stock solutions were serially diluted in the reaction buffer (50 mM Tris pH 7.5, 10 mM MgCl$_2$, 0.25 mM EGTA, 0.1 mM Na$_3$VO$_4$, 0.01% Triton X-100, 2.5 mM DTT). Recombinant kinases JAK1 (ProQinase), JAK2, or JAK3 (Carna Biosciences) were diluted in the dilution buffer (50 mM Tris-HCl pH 7.5, 150 mM NaCl, 10% glycerol, 0.05% Triton X-100, 1 mM DTT) to the final concentration 3 ng/μL (JAK1), 0.1 ng/μL (JAK2), or 0.2 ng/μL (JAK3). 5 μL of obtained solution of the compounds and 5 μL of the solution of respective kinases were added to the well of a 96-well plate. To initiate interaction between tested compounds and an enzyme, the plate was incubated for 10 minutes at 25° C. in a Plate-Thermo-Shaker with orbital stirring at 400 rpm. Wells of a negative control contained all reagents as mentioned above with the exception of tested compounds and kinase, and wells of a positive controls contained all reagents as mentioned above with the exception of tested compounds. Enzymatic reaction was initiated by the addition of 15 μL of the following solution: 5× concentrated reaction buffer (50 mM Tris pH 7.5, 10 mM MgCl$_2$, 0.25 mM EGTA, 0.1 mM Na$_3$VO$_4$, 0.01% Triton X-100, 2.5 mM DTT), water, 30 μM ATP and for particular kinases: JAK1—60 μM peptide IRS-1 (Enzo), JAK2 or JAK3—10 μM peptide IGF-1Rtide (Lipopharm). Then the plate was incubated for 1 hour at 25° C. in a Plate-Thermo-Shaker, with orbital stirring at 400 rpm. Detection of ADP formed in the enzymatic reaction was then performed using ADP-Glo Kinase Assay kit (Promega). For this purpose, to the well of the 96-well plate 25 μL of ADP-Glo Reagent were added, and the plate was incubated for 40 minutes at 25° C. in a Plate-Thermo-Shaker with orbital stirring at 400 rpm. Then to the well of the 96-well plate 50 μL of Kinase Detection Reagent were added and the plate was incubated for 30 minutes at 25° C. in a Plate-Thermo-Shaker with orbital stirring at 400 rpm. After incubation, luminescence intensity was measured using Victor×Light luminometer (Perkin Elmer, Inc.).

On the basis of luminescence measurement in wells containing tested compounds at various concentrations and in control wells, IC50 values were determined. These values were determined with Graph Pad software v. 5.03, by fitting points of the curve using non-linear regression method. Each compound was tested in at least 6 repetitions (6 wells) on two 96-well plates, using at least 3 wells of each control.

Averaged results of kinases JAK inhibition activity for selected compounds of the present invention are presented below in Table 1. Presented data show that compounds of the invention are able to inhibit JAK1 and JAK3 kinases preferentially over kinase JAK2.

TABLE 1

| Example No. | JAK1 IC$_{50}$ [nM] | JAK2 IC$_{50}$ [nM] | JAK3 IC$_{50}$ [nM] |
|---|---|---|---|
| 1 | 1.80 | 19.01 | 1.2 |
| 2 | 3.74 | 59.28 | 3.77 |
| 3 | 4.47 | 31.15 | 1.58 |
| 4 | 2.67 | 27.66 | 2.67 |
| 5 | 8.08 | 34.38 | 1.8 |
| 6 | 0.38 | 2.98 | 0.16 |
| 7 | 0.75 | 3.40 | 0.19 |
| 8 | 8.54 | 26.77 | 2.24 |
| 9 | 47.48 | 89.61 | 18.75 |
| 10 | 2.37 | 12.82 | 0.6 |
| 11 | 0.05 | 1.18 | 0.03 |
| 12 | 0.51 | 5.05 | 0.29 |
| 13 | 0.51 | 2.82 | 0.2 |

Assay for TF-1 Cells Viability In Vitro

The effects of the activity of the compounds of the invention were tested in vitro using cells viability assay described below.

Tested compounds were dissolved in 100% DMSO, and obtained stock solutions were serially diluted in OptiMEM medium (Reduced Serum Medium-Thermo Fisher Scientific). TF-1 cells (DSMZ no.: ACC 334) in culture medium (80% RPMI 1640+20% FBS) ad in the presence of 5 ng/mL IL-3 or 20 ng/mL IL-4 were deposited on 96-well plates in the volume of 90 μl per well, 10 thousands of cells per well. To a well of the 96-well plate 10 μL of the prepared 10× stock solutions of the compounds. Cells on 96-well plates were incubated with the compounds for 72 hours at 37° C., 5% CO$_2$. Subsequently, viability of the cells was measured using ATPlite kit (Perkin Elmer). For this purpose, 50 μL of lysis buffer (mammalian cell lysis solution) were added to a well of the 96-well plate and the plate was incubated for 10 minutes at 25° C. in a plate thermo-shaker with orbital stirring at 600 rpm. Then to a well of the 96-well plate 50 µL of substrate (substrate solution) were added and incubated for 15 minutes at in dark, in a plate thermo-shaker with orbital stirring at 600 rpm. After incubation time, luminescence intensity in a well was measured using Victor×Light luminometer (Perkin Elmer, Inc.).

On the basis of luminescence intensity measurements in well containing tested compounds at various concentrations and in control wells EC50 values were determined. These values were determined with Graph Pad software v. 5.03, by fitting points of the curve using non-linear regression method. Each compound was tested in at least 6 repetitions (6 wells) on two 96-well plates, using at least 3 wells of each control.

Averaged results of activity of inhibition of viability of the cells TF-1 in the presence of IL-3 (JAK2 activation) or IL-4 (JAK1/JAK3 activation) for selected compounds of the present invention are presented below in Table 2. Presented data show that compounds of the invention are able to inhibit JAK kinases, and that more potent JAK1/JAK3 kinases inhibition over kinase JAK2 inhibition can be seen.

TABLE 2

| Example No. | JAK2 IL3 [nM] | JAK1,3 IL4 [nM] | JAK2/ JAK1,3 Ratio |
|---|---|---|---|
| 1 | 836.9 | 350.4 | 2.4 |
| 2 | 1199 | 242.1 | 5 |
| 3 | — | — | — |
| 4 | 707 | 69 | 10.3 |
| 5 | — | — | — |
| 6 | 3327 | 361.4 | 9.2 |
| 7 | 282.6 | 36.1 | 7.8 |
| 8 | 2025 | 203.4 | 10 |
| 9 | — | — | — |
| 10 | 1285 | 111.6 | 11.5 |
| 11 | 451.3 | 61.13 | 7.4 |
| 12 | 360.9 | 31.1 | 11.6 |
| 13 | 1121 | 201.7 | 5.6 |

Assay for Inhibition of TNFα and INFγ Production by Lymphocytes T In Vitro

The activity of the compounds of the invention was tested using in vitro assay described below.

Tested compounds were dissolved in 100% DMSO, and obtained stock solutions were serially diluted with OptiMEM medium (Reduced Serum Medium-Thermo Fisher Scientific). Lymhocytes were isolated from leukocyte top coat layer obtained from human peripheral blood. Isolation of peripheral blood mononuclear cells was performed using Ficoll-Paque+Leucosept gradient method, with lymphocytes isolation using CD4+ T Cell Isolation Kit, and activation using T Cell Activation/Expansion Kit (Miltenyi Biotec). Isolated cells in culture medium (90% RPMI 1640+ 10% FBS) were sived on 12-well plates at 450 µL/well, 300 thousands/well, and 50 µL of prepared 10× stock solutions of tested compounds were added. After 48 hours supernatant was collected for determination of the level of secreted cytokines. Before determination, cells were centrifuged at 1000 g, 10 min. Determination was performed with flow cytometer FACS Calibur using LEGENDplex Human Th cytokine kit. Results are presented in Table 3 as a percentage of inhibition of TNFα i INFγ cytokines secreted by lymphocytes T with reference to control cells.

TABLE 3

| Example No. | TNFα inhibition, % | | | INFγ inhibition, % | | |
|---|---|---|---|---|---|---|
| | 10 nM | 100 nM | 1000 nM | 10 nM | 100 nM | 1000 nM |
| 4 | 57.1 | 78.7 | 95.3 | 80.9 | 86.5 | 95.6 |
| 7 | 60.6 | 76.0 | 98.5 | 73.6 | 74.6 | 98.1 |
| 11 | 57.4 | 88.1 | 88.5 | 88.8 | 93.5 | 81.4 |
| 12 | 76.2 | 75.8 | 95.4 | 86.2 | 88.0 | 93.0 |

Assay of STAT6 Phosphorylation Inhibition In Vitro

The activity of the compounds of the invention was tested using in vitro assay described below.

Tested compounds were dissolved in 100% DMSO, and obtained stock solutions were serially in OptiMEM medium (Reduced Serum Medium-Thermo Fisher Scientific). TF-1 cells (DSMZ no.: ACC 334) in culture medium (80% RPMI 1640+20% FBS) in the presence of IL-4 at 20 ng/mL were sieved on 12-well plates at 900 µl/well, 700 thousands of cells/well. To a well of the 12-well plate 100 µL of obtained 10× solution of the compounds were added. Cells on 12-well plates were incubated with tested compounds for 1 hour at 37° C., 5% $CO_2$. Subsequently the cells were washed with PBS, lysed in RIPA buffer added with EDTA, proteases and phosphatases inhibitors, and incubated for 5 min on ice. Protein concentration was determined using Pierce BCA Protein Assay Kit (Thermo Fisher Scientific). Protein lysates were separated by electrophoresis (SDS-PAGE) on 8% polyacrylamide gels, then wet-transferred on nitrocellulose membrane and tested proteins were detected in accordance with the instructions of antibody manufacturer.

On the basis of the measurement of chemoluminescence intensity densitometric analysis was performed, results obtained for the cells treated with tested compounds at various concentrations were compared with those obtained for control cells, and $IC_{50}$ values were determined.

These values were determined with Graph Pad software v. 5.03, by fitting points of the curve using non-linear regression method. Each compound was tested in at least 3 repetitions. Averaged results of activity of inhibition of STAT6 protein phosphorylation in TF-1 cells in the presence of or IL-4 (JAK1/JAK3 activation) for selected compounds of the present invention are presented below in Table 4.

TABLE 4

| Example No. | $IC_{50}$ [nM] |
|---|---|
| 4 | 442.0 |
| 7 | 115.8 |
| 11 | 114.5 |
| 12 | 149.8 |
| 13 | 214.8 |

The invention claimed is:
1. A compound of the formula (I)

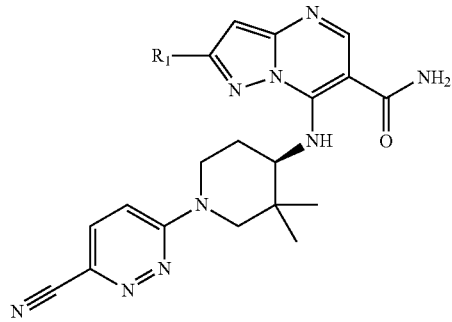

wherein R₁ represents:
  phenyl substituted with one or two substituents selected from the group consisting of halogen and C1-C3 alkoxy;
  or
  6-membered heteroaryl with 1 or 2 nitrogen atoms, which is unsubstituted or substituted with a substituent selected from the group consisting of:
    NH₂,
    halogen,
    alkyl C1-C4,
    alkoxyl C1-C3, and
    6-membered heterocyclyl comprising 1 or 2 heteroatoms selected from the group consisting of N and 0;
  or its acid addition salt.

2. The compound according to claim 1, wherein R₁ represents phenyl substituted with one or two substituents selected from the group consisting of halogen and C1-C3 alkoxyl.

3. The compound according to claim 1, wherein R₁ represents 6-membered heteroaryl with 1 or 2 nitrogen atoms, which is unsubstituted or substituted with a substituent selected from the group consisting of:
  NH₂,
  halogen,
  alkyl C1-C4,
  alkoxyl C1-C3, and
  6-membered heterocyclyl comprising 1 or 2 heteroatoms selected from the group consisting of N and 0.

4. The compound according to claim 3, wherein said heteroaryl is pyridinyl.

5. The compound according to claim 3, wherein said heteroaryl is pyrimidinyl.

6. The compound according to claim 4, wherein said heteroaryl is substituted with a substituent selected from the group consisting of alkyl C1-C4, alkoxyl C1-C3, and 6-membered heterocyclyl comprising 1 or 2 heteroatoms selected from the group consisting of N and O.

7. The compound according to claim 4, wherein the pyridinyl is substituted with C1-C3 alkoxyl.

8. The compound according to claim 5, wherein the pyrimidinyl is substituted with C1-C3 alkoxyl.

9. The compound of claim 1, selected from the group consisting of the following:
  1) (R)-7-((1-(6-Cyanopyridazin-3-yl)-3,3-dimethylpiperidin-4-yl)amino)-2-(4-methoxyphenyl)pyrazolo[1,5-a]pyrimidine-6-carboxamide;
  2) (R)-7-((1-(6-Cyanopyridazin-3-yl)-3,3-dimethylpiperidin-4-yl)amino)-2-(2-fluoro-5-methoxyphenyl)pyrazolo[1,5-a]pyrimidine-6-carboxamide;
  3) (R)-7-((1-(6-Cyanopyridazin-3-yl)-3,3-dimethylpiperidin-4-yl)amino)-2-(pyridin-3-yl)pyrazolo[1,5-a]pyrimidine-6-carboxamide;
  4) (R)-7-((1-(6-Cyanopyridazin-3-yl)-3,3-dimethylpiperidin-4-yl)amino)-2-(6-methoxypyridin-3-yl)pyrazolo[1,5-a]pyrimidine-6-carboxamide;
  5) (R)-7-((1-(6-Cyanopyridazin-3-yl)-3,3-dimethylpiperidin-4-yl)amino)-2-(6-ethoxypyridin-3-yl)pyrazolo[1,5-a]pyrimidine-6-carboxamide;
  6) (R)-2-(6-Aminopyridin-3-yl)-7-((1-(6-cyanopyridazin-3-yl)-3,3-dimethylpiperidin-4-yl)amino)pyrazolo[1,5-a]pyrimidine-6-carboxamide;
  7) (R)-7-((1-(6-Cyanopyridazin-3-yl)-3,3-dimethylpiperidin-4-yl)amino)-2-(6-morpholinopyridin-3-yl)pyrazolo[1,5-a]pyrimidine-6-carboxamide;
  8) (R)-7-((1-(6-Cyanopyridazin-3-yl)-3,3-dimethylpiperidin-4-yl)amino)-2-(2-methoxypyrimidin-5-yl)pyrazolo[1,5-a]pyrimidine-6-carboxamide;
  9) (R)-7-((1-(6-Cyanopyridazin-3-yl)-3,3-dimethylpiperidin-4-yl)amino)-2-(2-ethoxypyrimidin-5-yl)pyrazolo[1,5-a]pyrimidine-6-carboxamide;
  10) (R)-7-((1-(6-Cyanopyridazin-3-yl)-3,3-dimethylpiperidin-4-yl)amino)-2-(6-fluoropyridin-3-yl)pyrazolo[1,5-a]pyrimidine-6-carboxamide;
  11) (R)-7-((1-(6-Cyanopyridazin-3-yl)-3,3-dimethylpiperidin-4-yl)amino)-2-(6-methoxypyridin-2-yl)pyrazolo[1,5-a]pyrimidine-6-carboxamide;
  12) (R)-7-((1-(6-Cyanopyridazin-3-yl)-3,3-dimethylpiperidin-4-yl)amino)-2-(2-methylpyridin-4-yl)pyrazolo[1,5-a]pyrimidine-6-carboxamide;
  13) (R)-7-((1-(6-Cyanopyridazin-3-yl)-3,3-dimethylpiperidin-4-yl)amino)-2-(2-morpholinopyridin-4-yl)pyrazolo[1,5-a]pyrimidine-6-carboxamide; and
  acid addition salts thereof.

10. The compound according to claim 1, which is (R)-7-((1-(6-cyanopyridazin-3-yl)-3,3-dimethylpiperidin-4-yl)amino)-2-(6-methoxypyridin-2-yl)pyrazolo[1,5-a]pyrimidine-6-carboxamide or an acid addition salt thereof.

11. A pharmaceutical composition comprising as an active ingredient the compound of claim 1 and a pharmaceutically acceptable carrier or excipient.

12. A method of treatment of chronic inflammatory and autoimmunological diseases in a mammalian subject comprising administering to said mammalian subject a therapeutically effective amount of the compound as defined in claim 1.

13. A pharmaceutical composition comprising as an active ingredient the compound of claim 9 and a pharmaceutically acceptable carrier or excipient.

14. A pharmaceutical composition comprising as an active ingredient the compound of claim 10 and a pharmaceutically acceptable carrier or excipient.

15. A method of treatment of chronic inflammatory and autoimmunological diseases in a mammal subject comprising administering to said subject a therapeutically effective amount of the compound as defined in claim 9.

16. A method of treatment of chronic inflammatory and autoimmunological diseases in a mammal subject comprising administering to said subject a therapeutically effective amount of the compound as defined in claim 10.

17. The compound of claim 1, which is (R)-7-((1-(6-Cyanopyridazin-3-yl)-3,3-dimethylpiperidin-4-yl)amino)-2-(6-methoxypyridin-2-yl)pyrazolo[1,5-a]pyrimidine-6-carboxamide hydrochloride.

18. A pharmaceutical composition comprising as an active ingredient the compound of claim 17 and a pharmaceutically acceptable carrier or excipient.

19. The compound according to claim 7, wherein the pyridinyl is pyridin-2-yl, pyridin-3-yl or pyridin-4-yl.

20. The compound according to claim 8, wherein the pyrimidinyl is pyrimidin-5-yl.

* * * * *